US007955362B2

(12) United States Patent  (10) Patent No.: US 7,955,362 B2
Erickson et al.  (45) Date of Patent: Jun. 7, 2011

(54) APPARATUS AND METHOD FOR BODY TISSUE FIXATION

(75) Inventors: Paul Lawrence Erickson, Eastlake, OH (US); Jason A. Lisy, Mentor, OH (US); Stephanie Adi Soulen Harrington, Mentor, OH (US); Isador H. Lieberman, Pepper Pike, OH (US); Stephen Edward Keverline, Mentor, OH (US)

(73) Assignees: Merlot Orthopedix Inc., Mentor, OH (US); The Cleveland Clinic Foundation, Cleveland, OH (US)

( * ) Notice: Subject to any disclaimer, the term of this patent is extended or adjusted under 35 U.S.C. 154(b) by 513 days.

(21) Appl. No.: 11/781,017

(22) Filed: Jul. 20, 2007

(65) Prior Publication Data

US 2008/0097444 A1  Apr. 24, 2008

Related U.S. Application Data

(60) Provisional application No. 60/832,417, filed on Jul. 21, 2006.

(51) Int. Cl.
*A61B 17/80* (2006.01)
*A61B 17/84* (2006.01)

(52) U.S. Cl. .................... 606/289; 606/280; 606/305

(58) Field of Classification Search ............. 411/114, 411/128, 326, 360–363, 961–962; 606/70–71, 606/280, 282–285, 287–288, 297–299, 75, 606/281, 286, 289–296, 301–302, 304, 325–331, 606/303, 305–324, 902–906
See application file for complete search history.

(56) References Cited

U.S. PATENT DOCUMENTS

| 174,175 A * | 2/1876 | Adgate ........................ 411/145 |
| 467,324 A * | 1/1892 | Raybuck ....................... 411/114 |
| 2,401,856 A * | 6/1946 | Brock ........................... 411/517 |
| 4,484,570 A | 11/1984 | Sutter et al. |
| 4,755,092 A * | 7/1988 | Yaniv ............................ 411/554 |
| 4,763,456 A * | 8/1988 | Giannuzzi ........................ 52/410 |
| 5,275,601 A * | 1/1994 | Gogolewski et al. ......... 606/291 |
| 5,931,838 A * | 8/1999 | Vito ............................. 606/281 |
| 6,227,782 B1 * | 5/2001 | Bowling et al. .............. 411/114 |
| 6,361,537 B1 * | 3/2002 | Anderson .................. 606/86 B |

(Continued)

FOREIGN PATENT DOCUMENTS

EP  1 776 928 A2  4/2007

(Continued)

*Primary Examiner* — Thomas C Barrett
*Assistant Examiner* — Larry E Waggle, Jr.
(74) *Attorney, Agent, or Firm* — Tarolli, Sundheim, Covell & Tummino LLP

(57) ABSTRACT

A body tissue fixation apparatus includes a plate having oppositely disposed outer and tissue-contacting surfaces, and at least one fixation hole extending between the outer and tissue-contacting surfaces along a longitudinal axis. The fixation hole is defined in part by an inner hole surface having at least one serration. At least one fixation device of the body tissue fixation apparatus has a shank and a head portion, the shank being insertable through the fixation hole in the plate to affix the plate to the body tissue member upon rotation of the head portion. At least one deformable member is connected to the head portion, the deformable member extending laterally in a direction substantially perpendicular to the longitudinal axis and being adapted to deflect to engage with at least one serration formed on the inner hole surface. A method for using the body tissue fixation apparatus is also described.

25 Claims, 21 Drawing Sheets

U.S. PATENT DOCUMENTS

| | | |
|---|---|---|
| 6,402,755 B1 | 6/2002 | Pisharodi |
| 7,229,442 B2 * | 6/2007 | Schafer .................. 606/272 |
| 7,322,273 B2 * | 1/2008 | Rafn ....................... 92/256 |
| 7,699,880 B2 * | 4/2010 | Orbay et al. ............. 606/290 |
| 2004/0127896 A1 * | 7/2004 | Lombardo et al. ........ 606/61 |
| 2004/0127904 A1 * | 7/2004 | Konieczynski et al. ... 606/70 |
| 2004/0260306 A1 * | 12/2004 | Fallin et al. ............. 606/104 |
| 2005/0096657 A1 * | 5/2005 | Autericque et al. ....... 606/69 |
| 2005/0192580 A1 | 9/2005 | Dalton |
| 2007/0073297 A1 * | 3/2007 | Reynolds ................. 606/69 |
| 2009/0024170 A1 | 1/2009 | Kirschman |

FOREIGN PATENT DOCUMENTS

| | | |
|---|---|---|
| WO | WO 02/083014 A1 | 10/2004 |
| WO | WO 2004/112627 A2 | 12/2004 |
| WO | WO 2004112627 A2 * | 12/2004 |

* cited by examiner

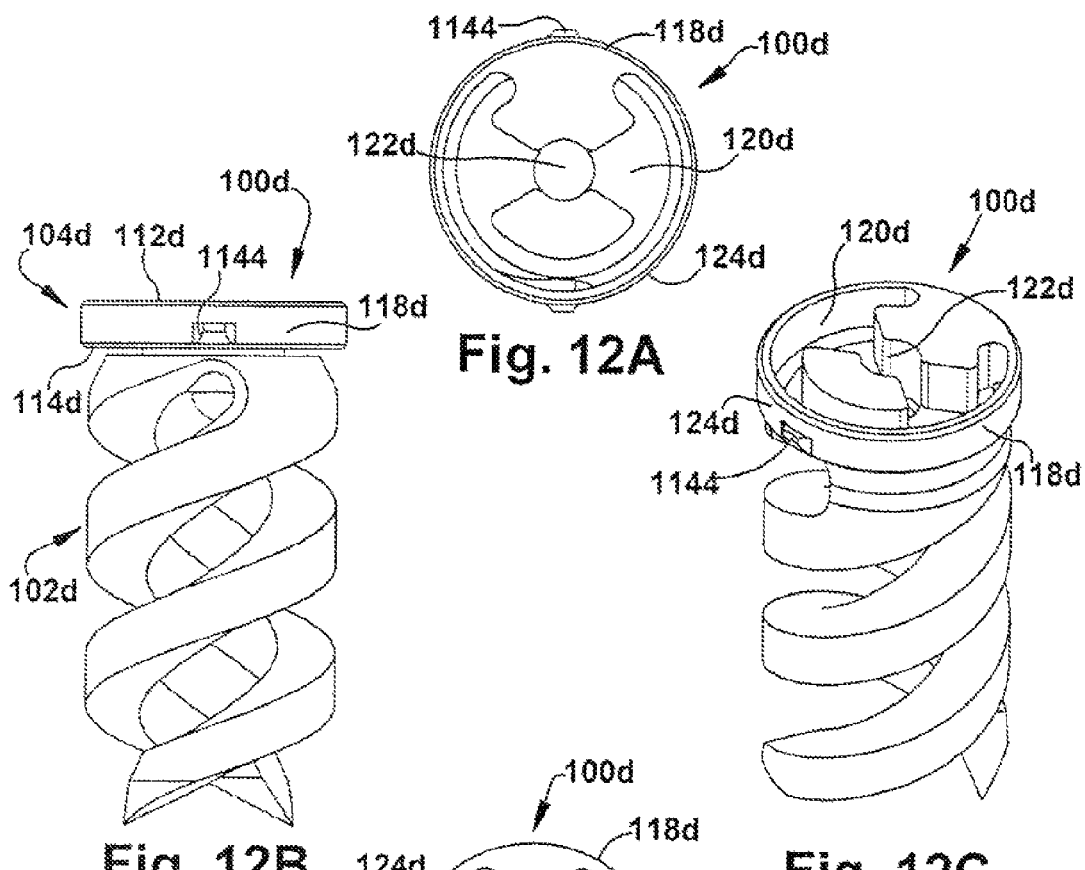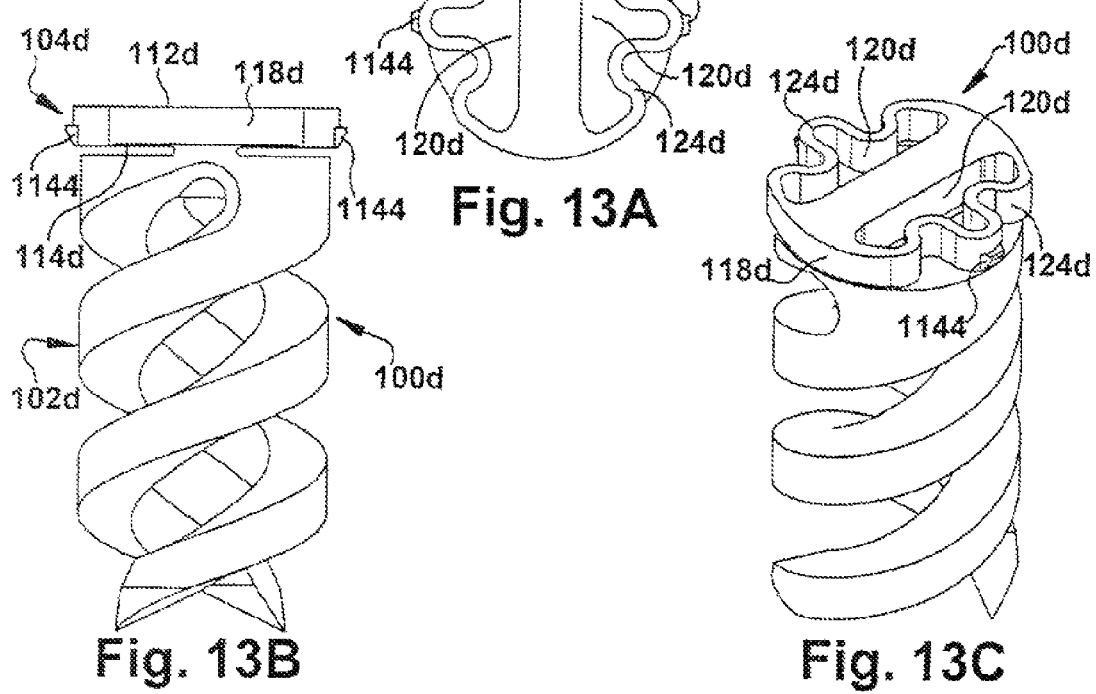

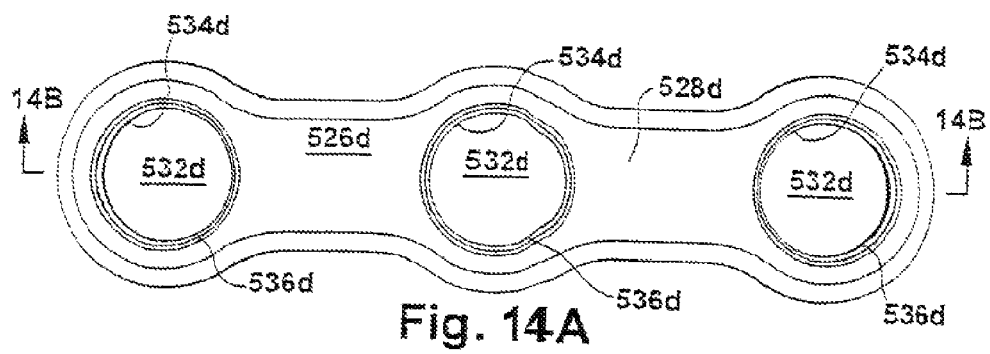
Fig. 14A
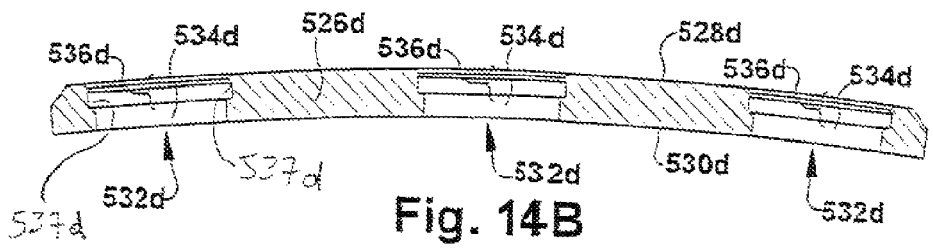
Fig. 14B
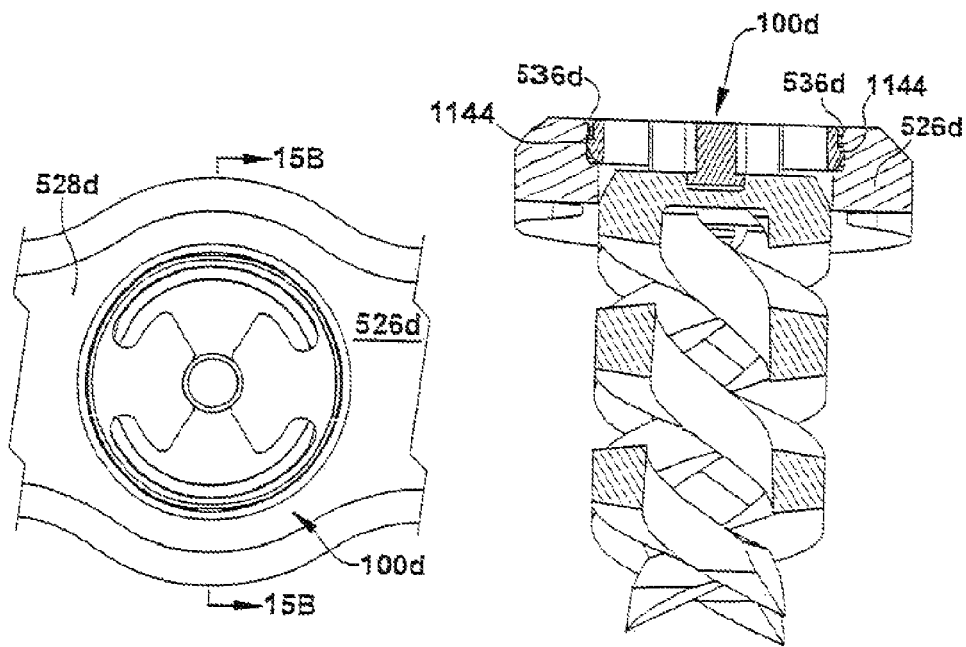
Fig. 15A
Fig. 15B

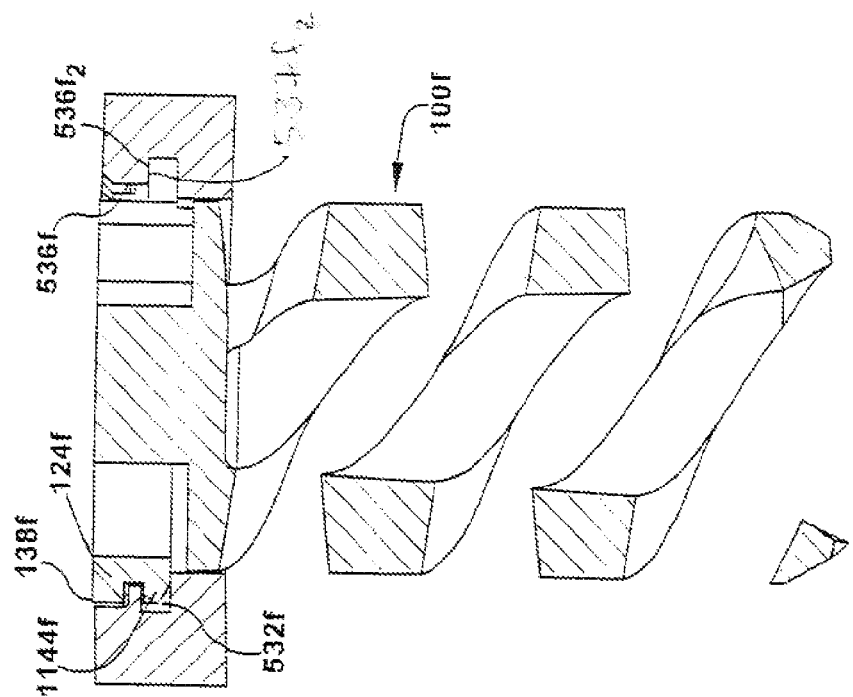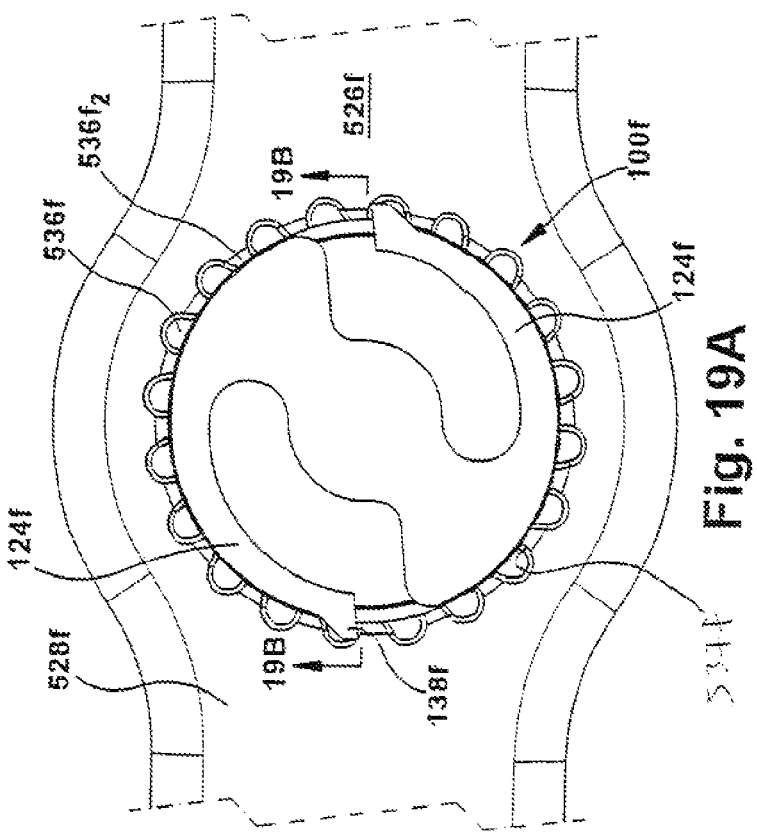

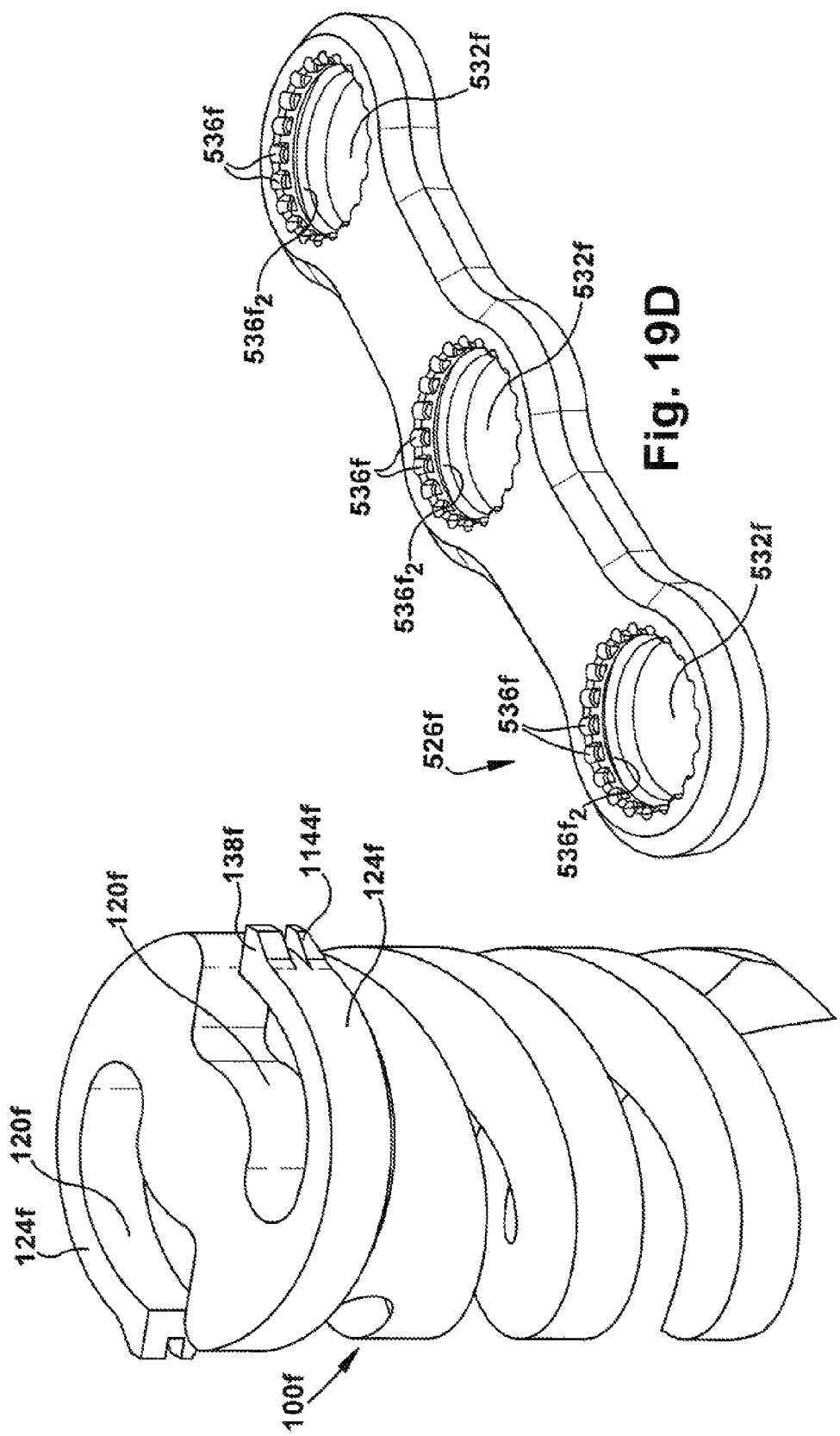

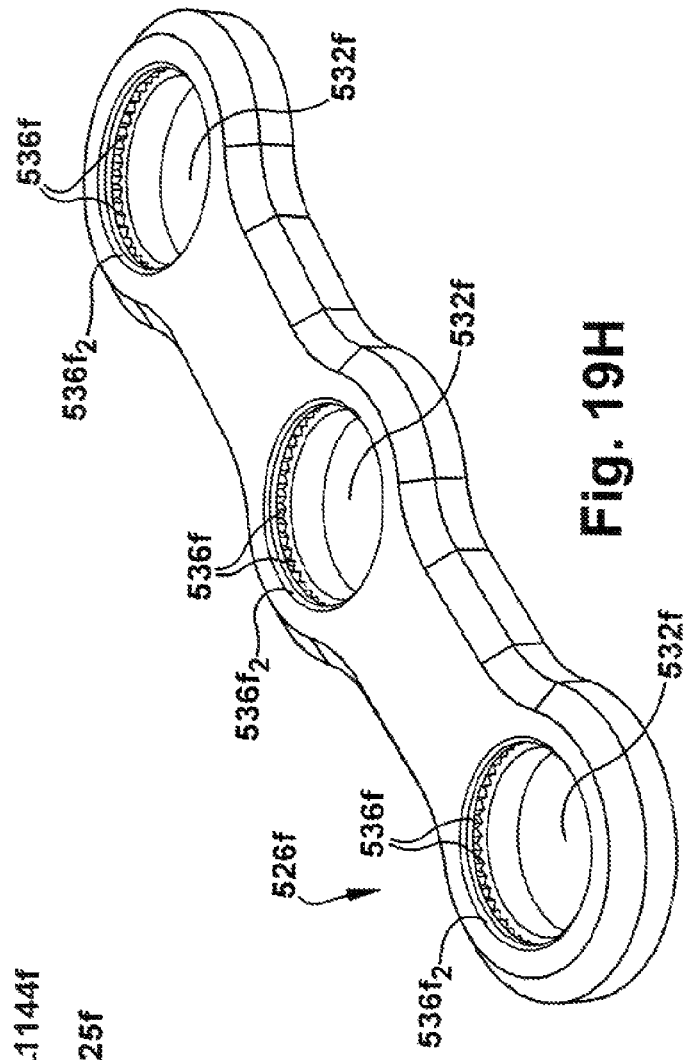
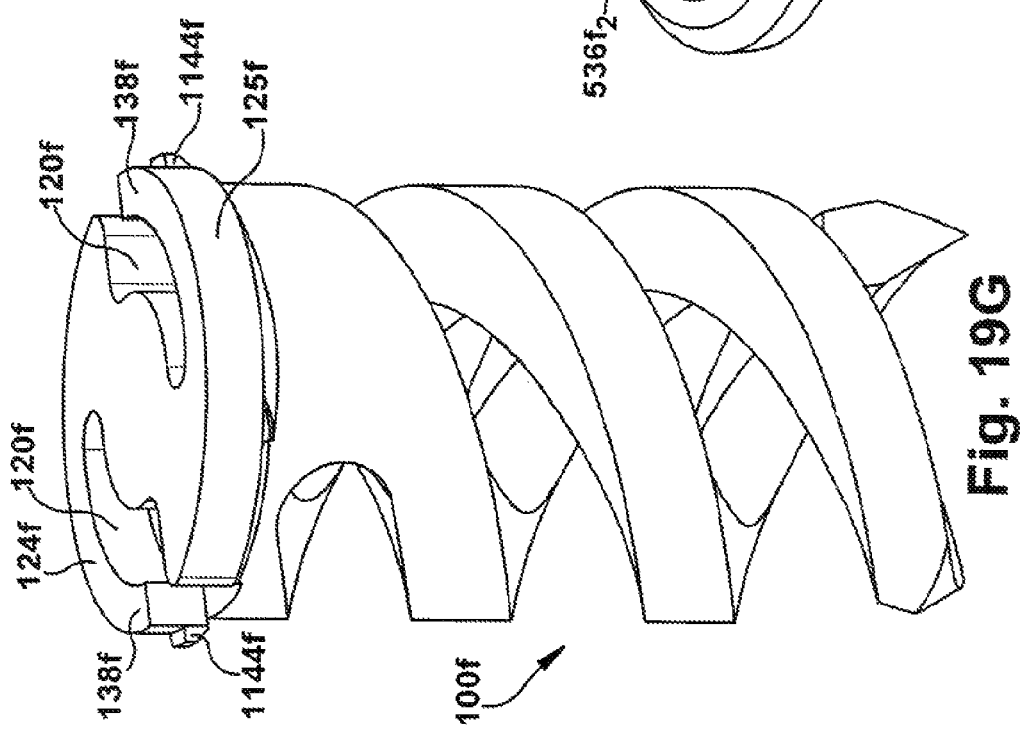

APPARATUS AND METHOD FOR BODY TISSUE FIXATION

This application claims priority from U.S. Provisional Application No. 60/832,417, filed Jul. 23, 2006, the subject matter which is incorporated herein by reference.

TECHNICAL FIELD

The present invention relates to an apparatus and method for affixing body tissue.

BACKGROUND OF THE INVENTION

Bone screws are used in the medical field for a variety of purposes. Typical uses for bone screws, which may be also referred to as bone anchors and will be discussed as such below, include treating a bone fracture, attaching a corrective device to parts of a fractured bone in an area adjacent to the fracture, and attaching a corrective device to a group of bones. For example, bone screws could be used to attach a plate to one or more vertebrae of a spinal column, such as in one or more of the anterior cervical, anterior or lateral thoracic, anterior or lateral lumbar, anterior lumbosacral or anterior sacral positions.

Bone screws may be used to mount suitable instrumentation—such as clamps, rods, and plates—to bones or other body tissues. Unfortunately, many of the known bone screws can be susceptible to toggling within the body tissue and can also pull out of the body tissue longitudinally due to the substantial forces on the screws from human body movement and muscle memory. So order to achieve a high pull-out resistance, it is known to thread a bone screw all of the way through a bone and place a nut on the opposite side. However, use of such a nut increases the complexity of the surgical procedure and may not be possible in a desired application if access to the opposing side of the bone is limited.

Additionally, known bone screws have a tendency to work free from the bone by rotating in a direction opposite the insertion rotation direction, thereby "backing out" of engagement with the bone and any corrective device through which the bone screw extends. Though this backward rotation differs from pullout due to toggling, the end result is still an undesirable displacement of the bone screw from the bone and/or an associated corrective device, which may necessitate additional surgeries and cause renewed patient trauma.

U.S. Pat. No. 4,484,570, issued Nov. 27, 1984 to Franz Sutter et al. (hereafter referenced as "the '570 patent") discloses a plate provided with clearance holes and fastening screws (Abstract). The fastening screw of the '570 patent is provided with a slotted clamping part and an expander (Col. 3, lines 21-23). The expander screws into the clamping part, thereby forcing the clamping part to splay outward and become fixedly engaged with the clearance hole (Col. 3, lines 29-32).

SUMMARY OF THE INVENTION

In an embodiment of the present invention, a body tissue fixation apparatus is described. The body tissue fixation apparatus includes a plate having oppositely disposed outer and tissue-contacting surfaces, and at least one fixation hole extending between the outer and tissue-contacting surfaces along a longitudinal axis. The fixation hole is defined in part by an inner hole surface having at least one serration. The plate is adapted for affixation to at least one body tissue member. At least one fixation device of the body tissue fixation apparatus has a shank and a head portion, the shank being insertable through the fixation hole in the plate to affix the plate to the body tissue member upon rotation of the head portion. At least one deformable member is connected to the head portion, the deformable member extending laterally in a direction substantially perpendicular to the longitudinal axis and being adapted to deflect to engage with at least one serration formed on the inner hole surface. Engagement between the deformable member and the serration helps to prevent displacement of the fixation device within the fixation hole.

In an embodiment of the present invention, a method for securing a plate to a body tissue of a patient is described. A plate having oppositely disposed outer and tissue-contacting surfaces and at least one fixation hole extending between the outer and tissue-contacting surfaces along a longitudinal axis is provided. The fixation hole is defined in part by an inner hole surface having at least one serration. The plate is placed into a desired orientation with the body tissue. At least one fixation device having a shank with spaced-apart first and second shank ends separated along the longitudinal axis is provided. The fixation device has a head portion having top and bottom surfaces spaced apart by a main body. The first shank end extends from the bottom surface. The head portion includes at least one void extending longitudinally through the head portion body between the top and bottom head portion faces to define at least one deformable member extending from the main body. The second shank end is inserted into the fixation hole and into engagement with the body tissue. The head portion is rotated to cause the shank to sink into the body tissue and the head portion to engage the plate. The deformable member is deflected away from an initial position. A serration is engaged with the deformable member to help prevent the fixation device from displacement within the fixation hole.

BRIEF DESCRIPTION OF THE DRAWINGS

For a better understanding of the invention, reference may be made to the accompanying drawings, in which:

FIG. 12A is a top view of the fourth embodiment;

FIG. 12B is a side view of the fourth embodiment shown in FIG. 12A;

FIG. 12C is a perspective view of the fourth embodiment shown in FIG. 12A;

FIG. 13A is a top view of the fourth embodiment;

FIG. 13B is a side view of the fourth embodiment shown in FIG. 13A;

FIG. 13C is a perspective view of the fourth embodiment shown in FIG. 13A;

FIG. 14A is a top view of the fourth embodiment;

FIG. 14B is a cross-sectional view taken along line B-B in FIG. 14A;

FIG. 15A is a top view of the fourth embodiment;

FIG. 15B is a cross-sectional view taken along line B-B in FIG. 15A;

FIG. 19A is a top view of a sixth embodiment of the present invention;

FIG. 19B is a cross-sectional view taken along line B-B in FIG. 19A;

FIG. 19C is a perspective view of the sixth embodiment shown in FIG. 19A;

FIG. 19D is a perspective view of the sixth embodiment shown in FIG. 19A;

FIG. 19G is a perspective view of the sixth embodiment shown in FIG. 19E;

FIG. 19H is a perspective view of the sixth embodiment shown in FIG. 19E;

DESCRIPTION OF EMBODIMENTS

Figure 1A:
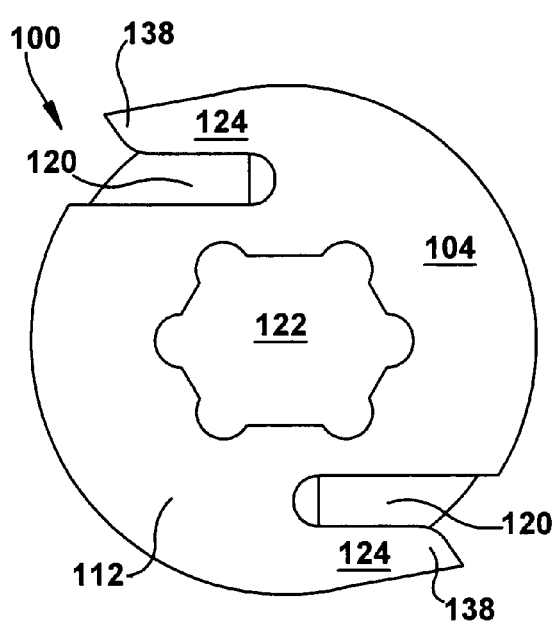
FIG. 1A is a top view of a first embodiment of the present invention.

In accordance with the present invention. FIGS. 1A, 1B, 2A, 2B, 3, 4, 5A, 5B, and 5C depict a body tissue fixation apparatus according to a first embodiment of the present invention. Though the present invention is described herein as being used with bone, the fixation apparatus of any embodiment of the present invention may be used with any suitable body tissue, such as, but not limited to, bone, tendons, fascia, cartilage, and dentin. The term "bone" is used throughout this description merely for clarity and ease of reference and does not restrict the potential use of the present invention in any desired application.

The fixation apparatus includes a fixation device 100 shown in FIGS. 1A, 1B, 2A, and 2B, which includes a shank 102 and a head portion 104. The shank 102 is adapted for engagement with a bone member (not shown) or other body tissue. The shank 102 has spaced-apart first and second shank ends 106 and 108, respectively, separated along a longitudinal axis 110. The longitudinal axis 110 defines a longitudinal direction. A transverse plane (not shown) may be defined as being substantially perpendicular to the longitudinal axis 110, at any point along the longitudinal axis. The term "laterally", used throughout this description, references an orientation substantially within or along the transverse plane. The term "radially" refers to a direction extending through the longitudinal axis.

The head portion 104 has top and bottom surfaces 112 and 114, respectively, spaced apart by a main body 116. The main body 116 is bounded laterally by a rim portion 118. The first shank end 106 extends from the bottom surface 114. The head portion 104 includes at least one void 120 extending longitudinally through the main body 116 between the top and bottom surfaces 112 and 114. The void 120 may extend completely through the main body 116, linking the top and bottom surfaces 112 and 114. The top and bottom surfaces 112 and 114 may be spaced apart along the longitudinal axis 110 and may each be substantially planar and parallel to each other.

Figure 2A:
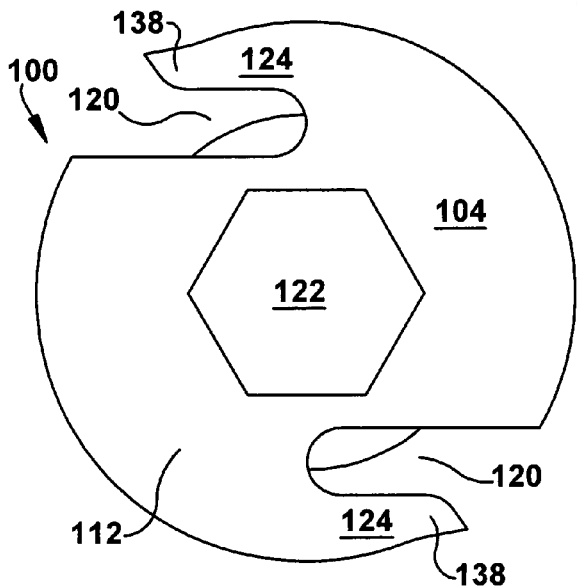
FIG. 2A is a top view, similar to FIG. 1A, of the first embodiment.

The head portion 104 may include a tool receptor void 122 extending from the top surface 112 into the main body 116. The tool receptor void 122 may extend from the top surface 112, through the main body 116 and the bottom surface 114, and into the first shank end 106. As shown in FIGS. 1A and 2A, the tool receptor void 122 may be configured to accept a standard or custom driving tool in a female-to-male manner. The driving tool may be an Allen wrench, Philips screwdriver, slotted screwdriver, TORX™ wrench, Robertson wrench, inside hex wrench, or any other suitable driving tool or combination thereof.

Figure 1B:
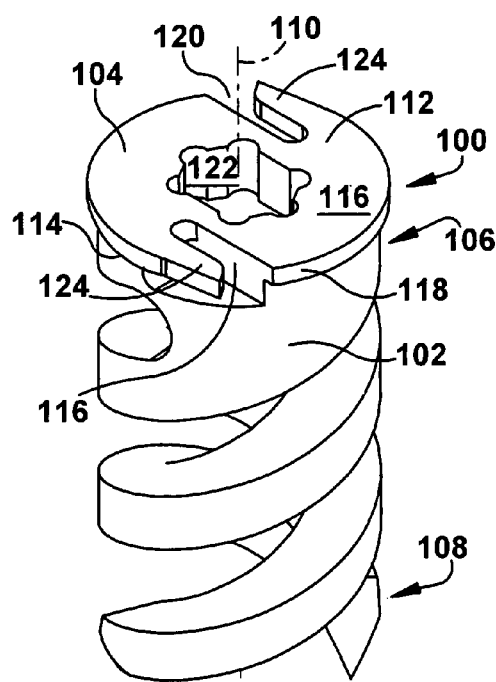
FIG. 1B is a perspective view of the first embodiment shown in FIG. 1A.
Figure 2B:
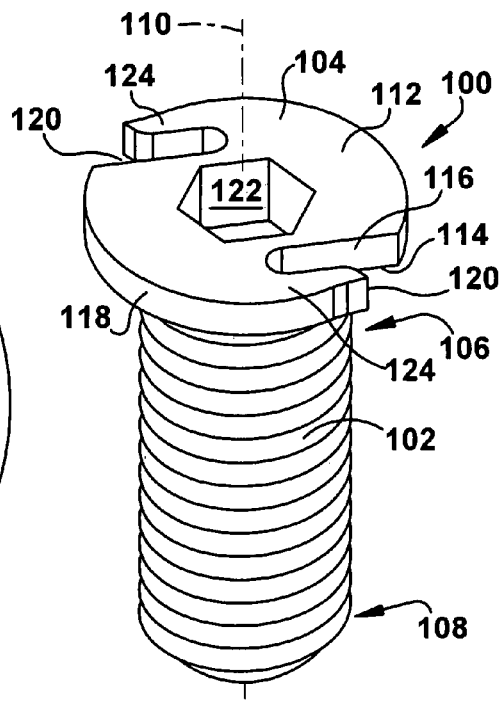
FIG. 2B is a perspective view, similar to FIG. 1B, of the first embodiment shown in FIG. 2A.

The shank 102 may be at least one helical spike, as shown in FIG. 1B, a threaded cylindrical post, as shown in FIG. 2B, or any other structure (not shown) suited to engage the bone in a desired manner. The shanks 102 shown in the figures are adapted for rotational driving into the bone and are described as such, but a spike, tack, or other percussion-driven shank 102 may also or instead be used in accordance with the present invention. Though the following description presumes a
rotation-driven shank 102, one of ordinary skill in the art could readily modify the described structure, according to the present invention, for use with a percussion-driven shank.

At least one deformable member 124 may be connected to the head portion 104. The term "deformable" means that the member 124 is capable of permanent/plastic deformation, temporary/elastic deformation, or a combination thereof in response to an applied force. Additionally, an elastically deformable member 124 naturally exerts a biasing force toward its original "resting" structural configuration when forced away from such configuration. The deformable member 124 extends laterally in a direction. Substantially perpendicular to the longitudinal axis 110 and is adapted to selectively deflect with respect to the longitudinal axis. The deformable member 124 may be formed integrally as a single piece with the head portion 104, as shown in at least FIGS. 1A, 1B, 2A, and 2B, or may be part of a separate structure connected to the head portion, as shown in at least FIGS. 6A, 6B, and 7, and discussed in detail below with respect to those figures. The deformable member 124 may be structurally defined, at least in part, by one or more of the void 120 and the rim portion 118. In the first embodiment, shown in FIGS. 1A, 1B, 2A, 2B, 3, 4, 5A, 5B, and 5C, the deformable member 124 is a cantilevered pawl 124 extending between the top and bottom surfaces 112 and 114. The void 120 may be shaped, configured, and sized as needed to create the deformable member 124 in a desired manner. The void 120 may have a cross-sectional shape which varies responsive to the longitudinal position of the cross-section within the main body 116. For example, and as shown in at least FIG. 1B, the void 124 may be designed with an L-shaped cross-section to fully free a bottom side of the cantilevered portion of the deformable-member 124 from the head portion 104.

Figure 3:
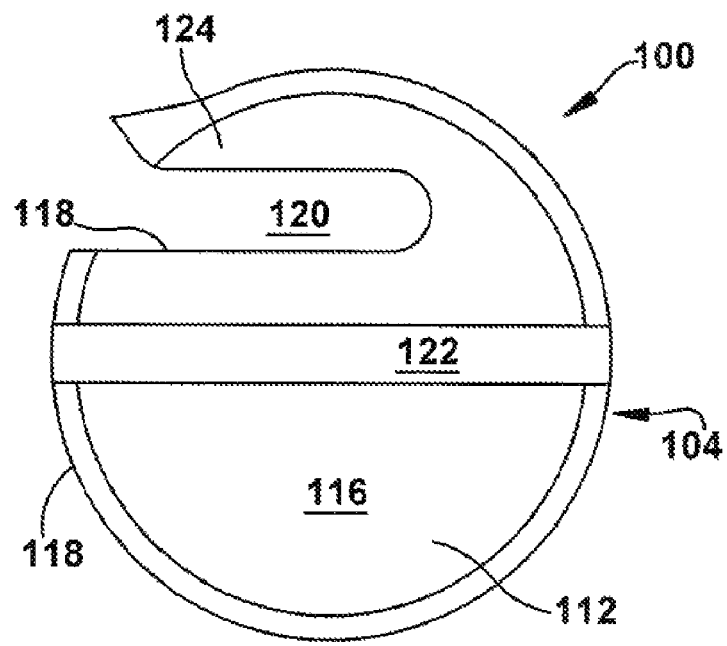
FIG. 3 is a top view, similar to FIG. 1A, of the first embodiment.
Figure 4:
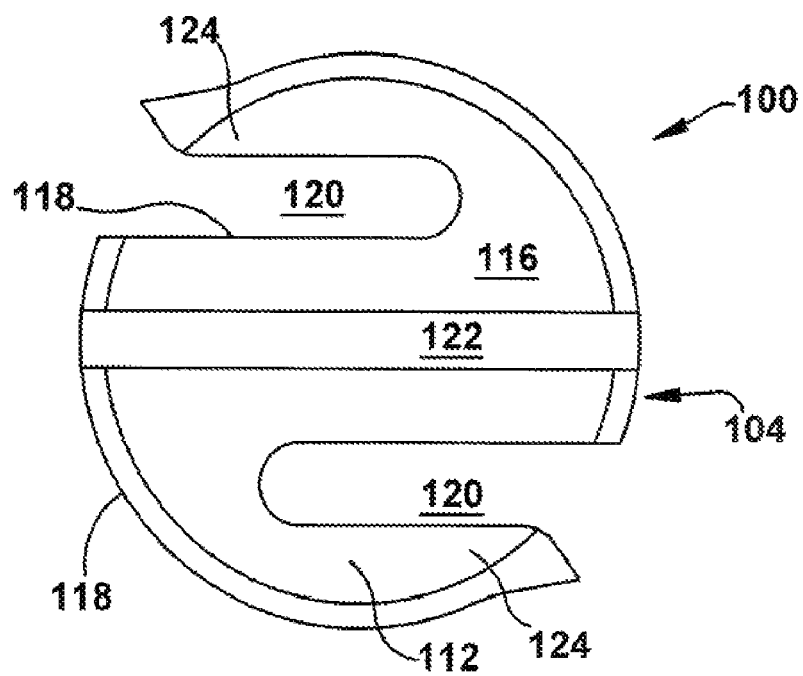
FIG. 4 is a top view, similar to FIG. 1A, of the first embodiment.
Figure 8:
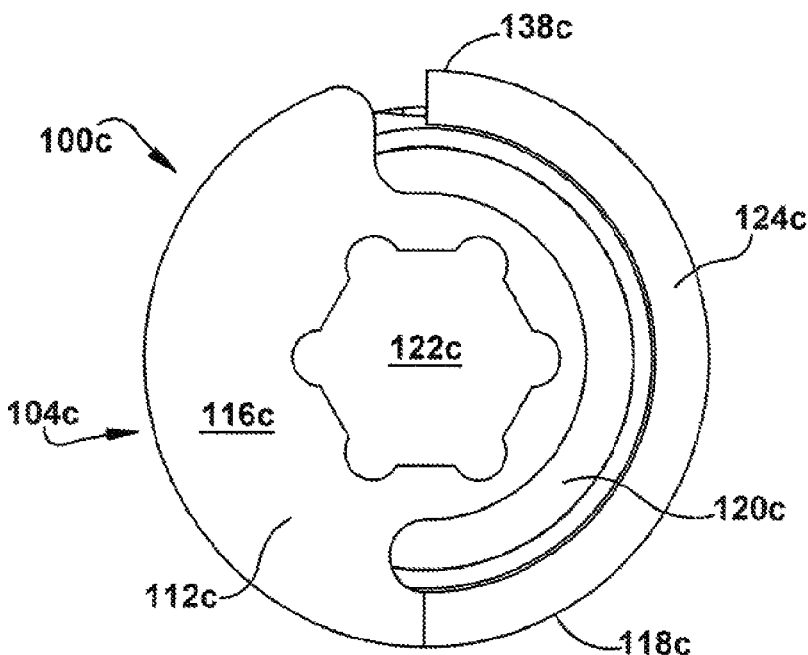
FIG. 8 is a top view of a third embodiment of the present invention.

The deformable member(s) 124 provided for the fixation device 100 may be of any suitable number, size, shape, configuration, orientation, or relationship to the fixation device. At least FIGS. 3 and 8 depict examples of alternate configurations of deformable members 124 (straight and curved pawl designs, respectively) suitable for use with the present invention, though a number of non-depicted configurations are possible and fall within the scope of the appended claims.

Figure 5A:
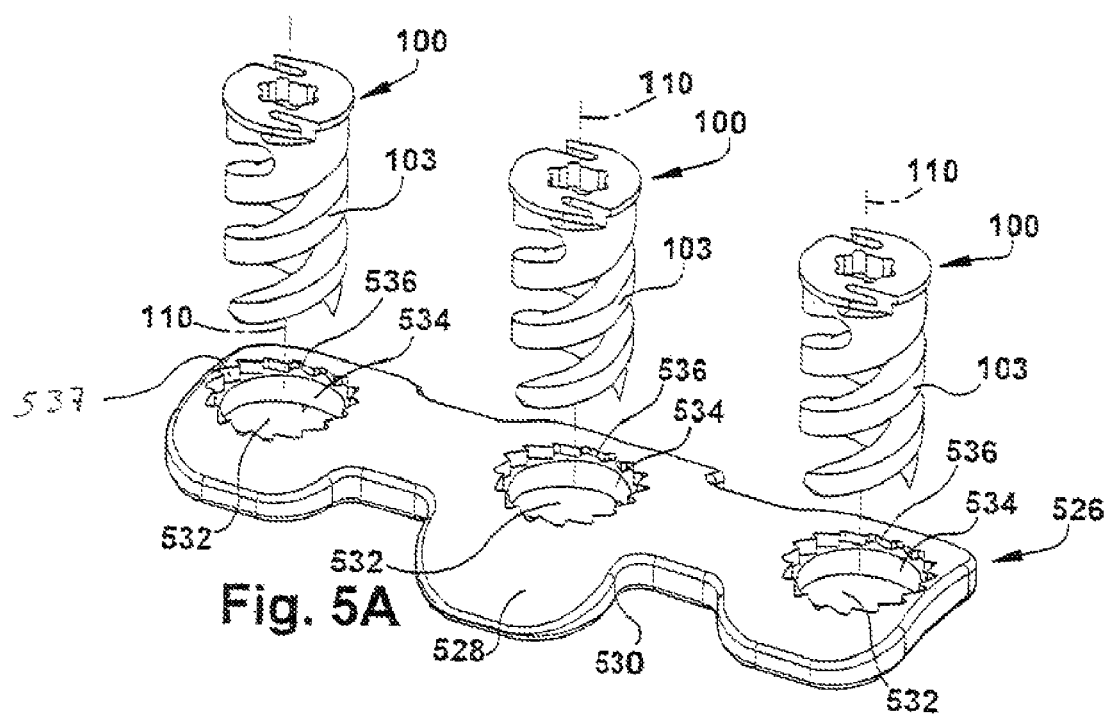
FIG. 5A is an exploded perspective view of the first embodiment.
Figure 5B:
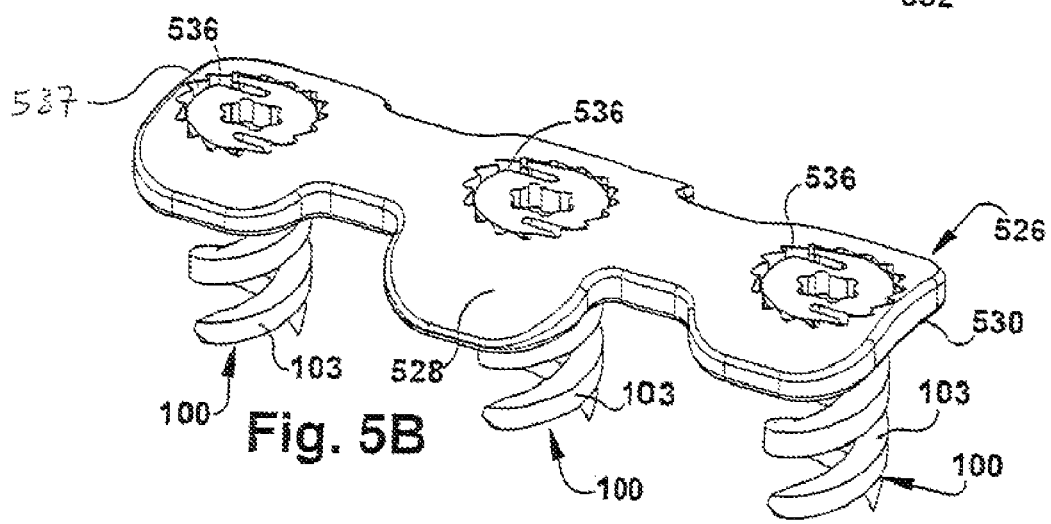
FIG. 5B is a perspective view of the first embodiment shown in FIG. 5A.
Figure 5C:
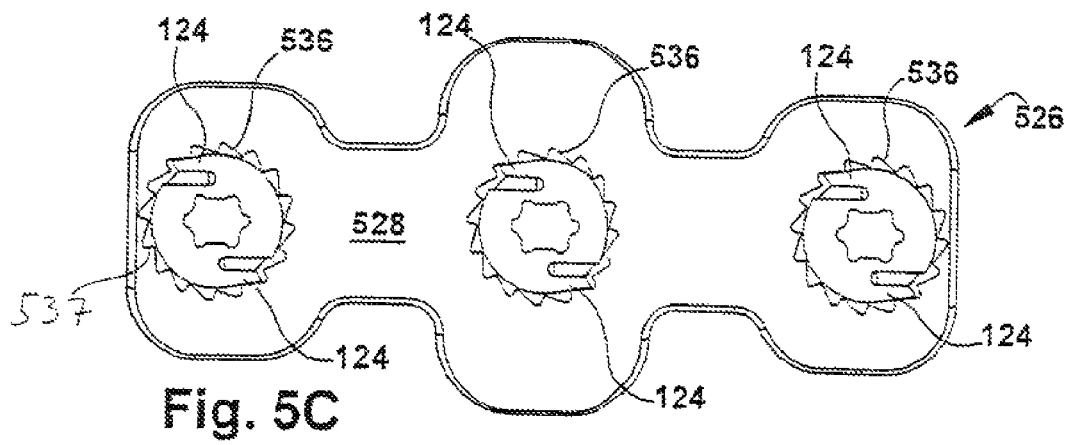
FIG. 5C is a top view of the first embodiment shown in FIG. 5A.

FIGS. 5A, 5B, and 5C depict a plate 526 for use in the body tissue fixation apparatus of the present invention. The plate 526 has oppositely disposed outer and tissue-contacting surfaces 528 and 530, respectively. The plate 526 may include one or more positioning spikes or tool engagement voids (not shown) to assist in holding the plate 526 in position temporarily while the fixation device 100 is being prepared and installed. The plate 526 shown in the Figures is of a type which is suitable for affixation to at least one bone member (not shown), but the specific structure of the plate does not restrict the present invention. Many other plate configurations and structures may be used with the fixation system described herein for applications using any suitable body tissue.

The plate 526 has at least one fixation hole 532 (three shown in FIGS. 5A, 5B, and 5C) extending between the outer and tissue-contacting surfaces 528 and 530 along a longitudinal axis 110. Each fixation hole 532 is defined in part by an inner hole surface 534 having at least one serration 536. When more than one serration 536 is present, the serrations may be oriented in different directions, as desired. The serrations 536 of a single plate 526 need not match each other in size, orientation, configuration, or any other property.

In the first embodiment of the present invention, as shown in FIGS. 5A-5C, each serration 536 is oriented longitudinally along the inner hole surface 534 and is spaced apart from at least one other serration along the inside diameter of the fixation hole 532. Each serration 536 extends at least a portion of the distance longitudinally between the outer and tissue-contacting surfaces 528 and 530 of the plate 526. A serration anti-reverse feature 537 is oriented to resist force exerted in a circumferential direction with respect to the longitudinal axis 110.

The shank 102 of the fixation device 100 is insertable through the fixation hole 532 in the plate 526 to affix the plate to the bone member upon rotation of the head portion 104. As shown in FIGS. 5A and 5B, the shank 102 may include a plurality of helical spikes 103 which can be screwed into the bone member. A removable jig (not shown) may surround the shank during installation to help prevent the helical spikes 103 from splaying outward under the driving force instead of biting into the bone member. The jig could be a bushing, a clamshell-type retaining jaw, or any other suitable structure. The jig should be chosen to fit closely enough around the helical spikes 103 to prevent splaying in a desired manner. The jig could act as a guide bushing to direct the angle, depth or another attribute of the installation of the fixation device 100 in a desired manner.

The deformable members 124 of each embodiment of the present invention are adapted to deflect to engage with at least one serration 536 formed in any suitable orientation on the inner hole surface 534. Engagement, between the deformable member 124 and the serration 536 helps to prevent displacement of the fixation device 100 within the fixation hole 532. More specifically, this engagement may be between the deformable member 124 and the serration anti-reverse feature 537. During this engagement, and as shown in at least FIG. 5C, the deformable member 124 extends to a location radially further from the longitudinal axis 110 than the location of at least a portion of the serration anti-reverse feature 537. In other words, the deformable member extends beyond a circumference of the non-deformable-member areas of the head portion 104 to "enter into" the serration 536.

More particularly, the deformable member 124 of the first embodiment is adapted to exert a spring force laterally outward from the longitudinal axis 110 to urge a tip 138 (see FIGS. 1A and 2A) of the deformable member 124 into engagement with at least one serration 536. This engagement between the deformable member 124 and the serration 536 helps to prevent the fixation device 100 from movement away from the bone member in a direction parallel to and/or lateral to the longitudinal axis 110.

One example of such an engagement is shown in FIGS. 5B and 5C. The deformable members 124 extend laterally outward from the longitudinal axis 110, with the tips 138 of the deformable members 124 extending laterally outward further from the longitudinal axis 110 than do the areas of the rim portion 118 which are not associated with deformable members 124. This lateral protrusion of the tips 138 may provide a slight interference fit between the head portion 104 and the fixation hole 532 such that the deformable members 124 must be pressed laterally inward for the head portion 104 to enter the fixation hole 532. The structure and material of the deformable member resist this inward lateral pressure, urging the tips 138 laterally outward from the longitudinal axis and into engagement with at least one serration 536 in a ratcheting manner. There is interference (i.e., contact) between the tips 138 and each serration 536 as the tips ride over and clear each serration. However, in the final assembled state, there may or may not be an interference fit between the head portion 104 and the fixation hole 532.

In the first embodiment shown in FIGS. 5A, 5B, and 5C, the head portion 104 may be rotated in a first direction (clockwise, as shown here) to screw the shank 102 into the bone member and thus affix the plate 526 to the bone member. However, and as can be seen in top view in FIG. 5C, the serrations 536 and tips 138 of the first embodiment are configured and oriented to resist rotation of the fixation device 100 in a second direction (counter-clockwise, as shown here). Though the serrations 536 and tips 138 here are arranged to permit rotation in a first direction while resisting rotation in a second, opposite direction, one of ordinary skill in the art could readily design serrations and tips which permit rotation in the second direction while resisting rotation in the first direction or which resist rotation in both the first and second directions, depending upon the desired application of the present invention.

Figure 6A:
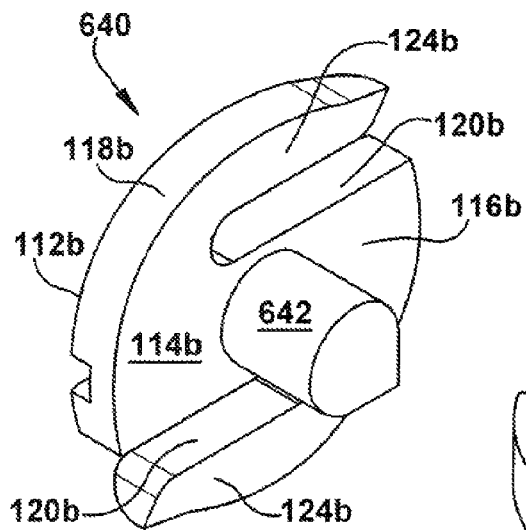
FIG. 6A is a perspective view of a second embodiment of the present invention.
Figure 6B:
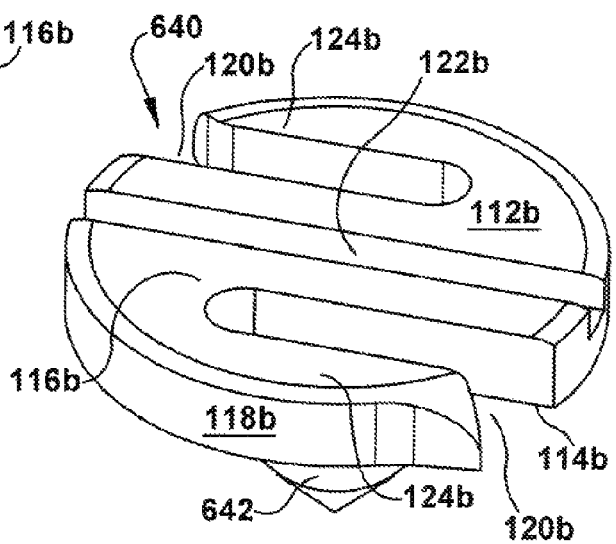
FIG. 6B is a perspective view of the second embodiment shown in FIG. 6A.
Figure 7:
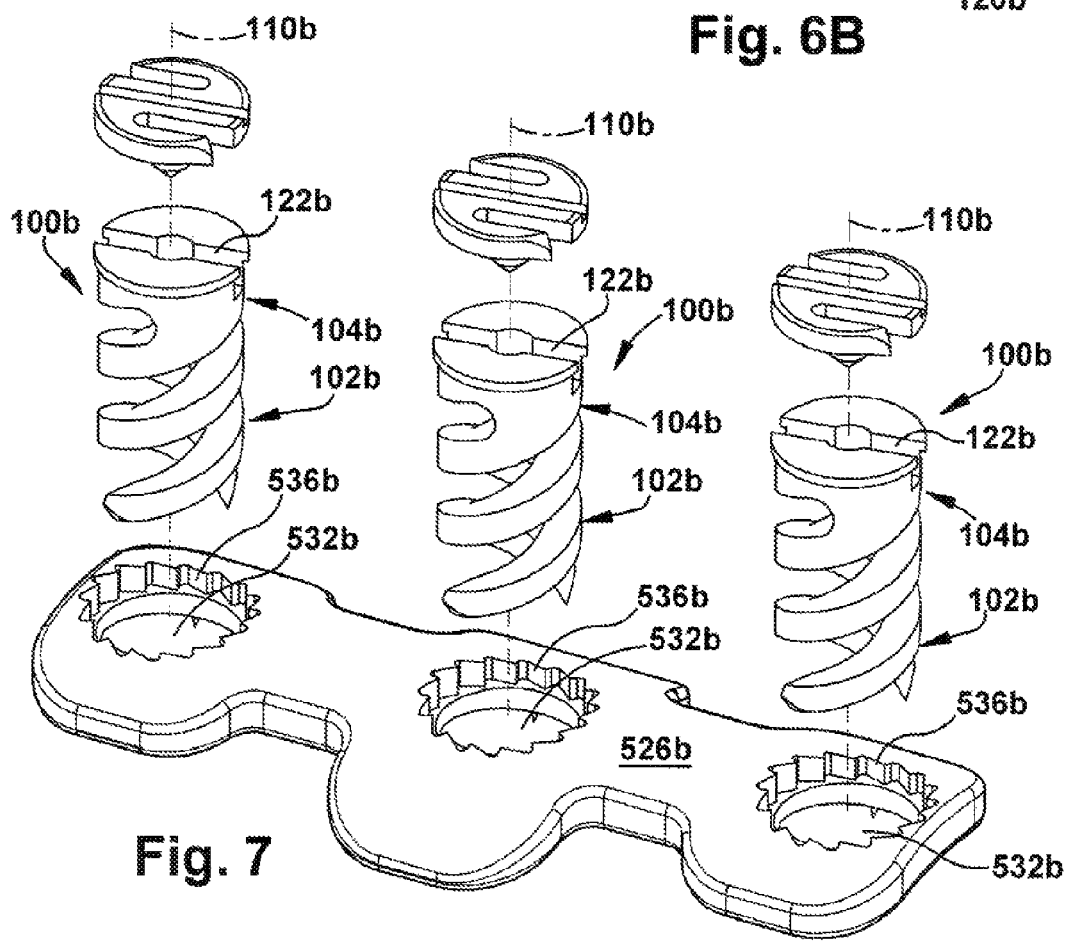
FIG. 7 is an exploded perspective view of the second embodiment.

FIGS. 6A, 6B, and 7 depict a fixation device 100b in accordance with a second embodiment of the present invention. Features of FIGS. 6A, 6B, and 7 that are the same as or similar to those described previously are given the same reference numbers with the addition of the suffix "b". Description of common elements and operation similar to those in the previously described embodiment will not be repeated with respect to the second embodiment.

FIGS. 6A and 6B depict a retainer button or cap 640 which is formed separately from the fixation device 100b. The retainer cap 640 includes at least one deformable member 124b which engages with at least one serration 536b of a fixation hole 532b to help prevent displacement of the fixation device 190b within the fixation hole 532b. The retainer cap 640 includes a retainer stud 642 adapted to mate with a tool engagement void 122b of the fixation device 100b and thereby connect the deformable member 124b of the retainer cap with the head portion 104b of the fixation device. The retainer stud 642 optionally includes threads (not shown) adapted to mate with corresponding threads of at least a portion of the tool engagement void 122b or another void or hole in the head portion 104b. Alternately, the retainer stud 642 could be affixed to the head portion 104b via an adhesive, interference fit, or any other suitable connection means.

FIGS. 8, 9A, 9B, 10A, 10B, and 10C depict a fixation device 100c in accordance with a third embodiment of the present invention. Features of FIGS. 8, 9A, 9B, 10A, 10B, and 10C that are the same as or similar to those described previously are given the same reference numbers with the addition of the suffix "c". Description of common elements and operation similar to those in the previously described embodiments will not be repeated with respect to the third embodiment.

Figure 9A:
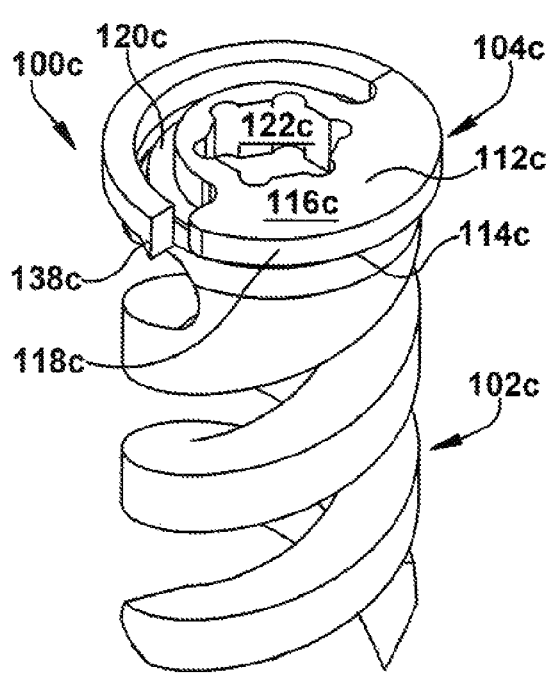
FIG. 9A is a perspective view of the third embodiment shown in FIG. 8.
Figure 9B:
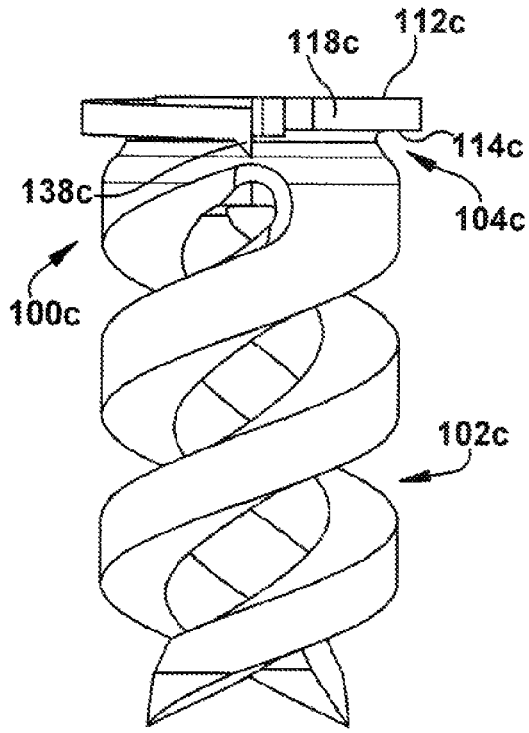
FIG. 9B is a side view of the third embodiment shown in FIG. 8.
Figure 10A:
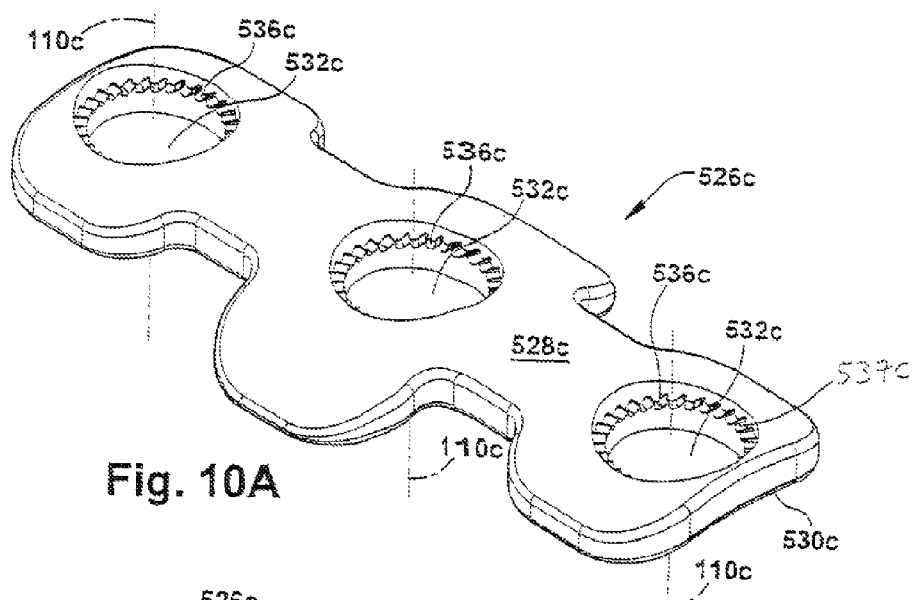
FIG. 10A is a perspective view of the third embodiment.
Figure 10B:
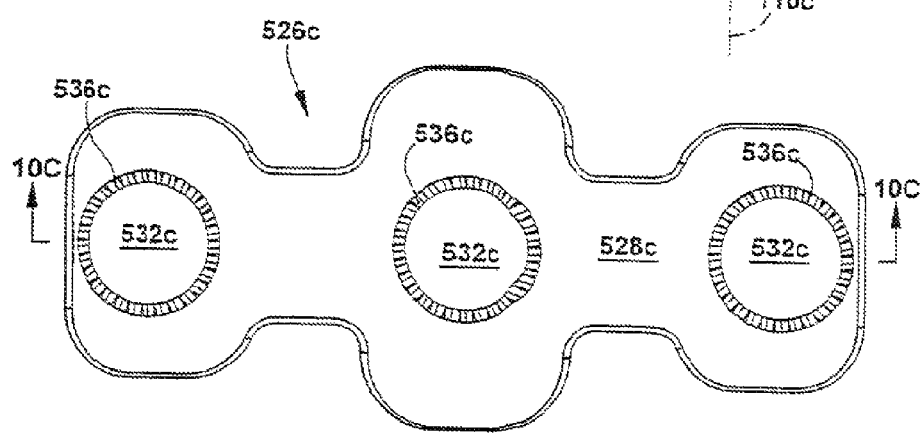
FIG. 10B is a top view of the third embodiment shown in FIG. 10A.
Figure 10C:
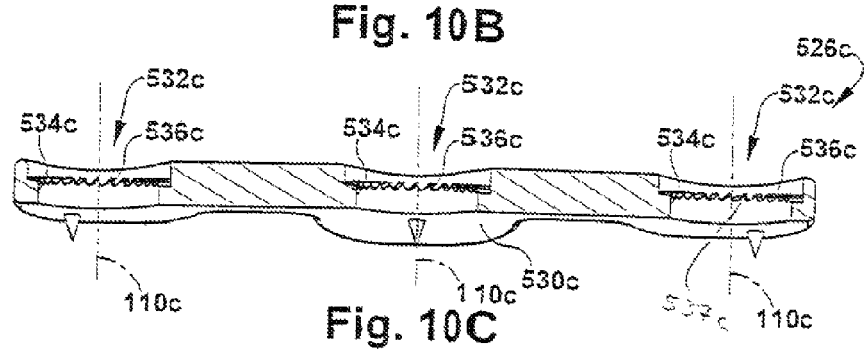
FIG. 10C is a sectional side view of the third embodiment shown in FIG. 10A.
Figure 11A:
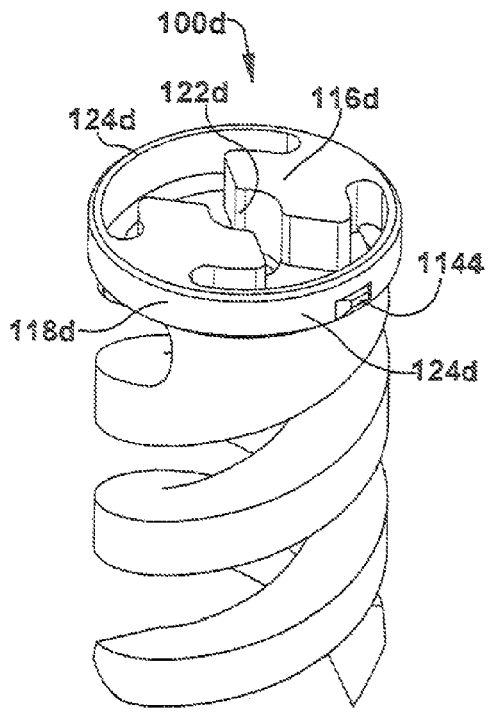
FIG. 11A is a perspective view of a fourth embodiment of the present invention.
Figure 11B:
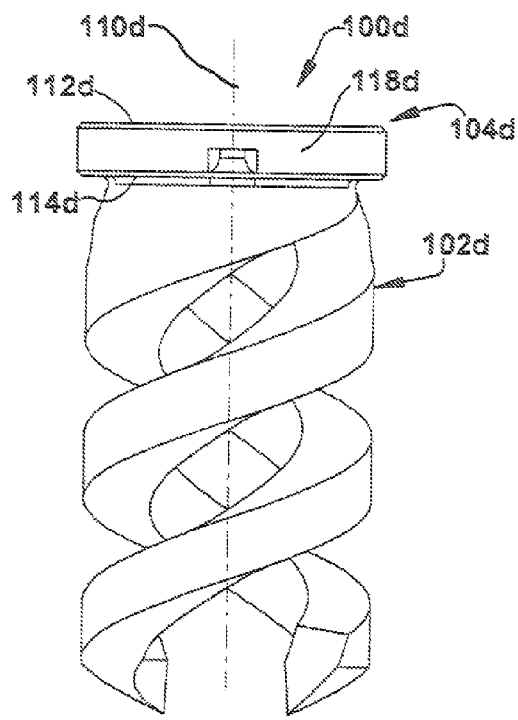
FIG. 11B is a side view of the fourth embodiment shown in FIG. 11A.
Figure 11C:
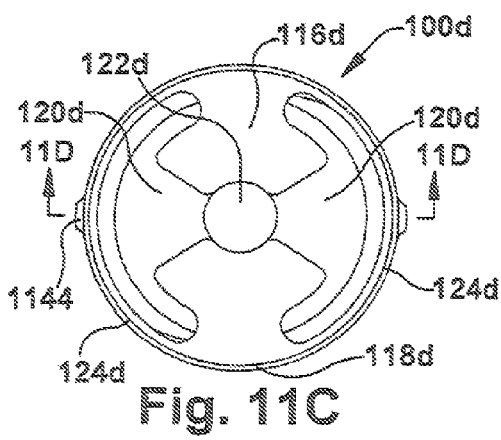
FIG. 11C is a top view of the fourth embodiment shown in FIG. 11A.
Figure 11D:
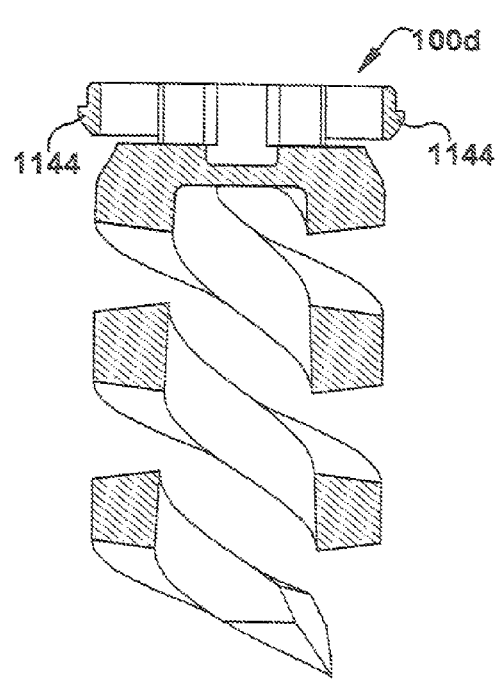
FIG. 11D is a cross-sectional view taken along line D-D in FIG. 11C.

The fixation device 100c shown in FIGS. 8, 9A, and 9B includes a deformable member 124c having a tip 138c protruding longitudinally toward the shank 102c. The plate 528c, shown in FIGS. 10A, 10B, and 10C, includes at least one serration 536c extending laterally with respect to the longitudinal axis 110c, with a plurality of serrations circumferentially spaced about a periphery of the fixation hole 532c to form a shelf-like array around the inner hole surface 534c, as depicted. A serration anti-reverse feature 537c is oriented to resist force exerted in a circumferential direction with respect to the longitudinal axis 110. As the fixation device 100c is inserted through the fixation hole 532c in the plate 528c, the deformable member 124c of the third embodiment deflects longitudinally: in a ratcheting manner to engage at least one serration 536c. During this engagement, the deformable member 124c extends to a location longitudinally further from the outer surface 528c of the plate 526c than the location of at least a portion of the serration anti-reverse feature 437c. In other words, the deformable member 124c extends deeper into the fixation hole 532c than do non-deformable-member areas of the head portion 104, causing the deformable member 124c to "enter into" the serration 536.

The engagement between the deformable member 124c and at least one serration 536c will resist displacement of the fixation device 100c by backing out due to rotation in a direction opposite the insertion direction. Should a longitudinal displacement force be exerted upon the fixation device 100c, however, the deformable member 124c may be shifted longitudinally and lose engagement with the serration 536c. Therefore, a holddown feature, similar to those discussed with respect to the sixth embodiment below, may be provided to exert a longitudinal pressure upon at least a portion of the deformable member 124c and thereby maintain engagement between the deformable member and at least one serration 536c. This holddown feature can be readily designed by one of ordinary skill in the art. Suitable holddown features may include, for example, a tooth formed integrally with the fixation device 100c or a separate snap ring or cover plate, any of which could be adapted to engage with a structure of the plate 526c, such as a serration, undercut, or pocket, and thereby help resist longitudinal displacement of the fixation device.

FIGS. 11A, 11B, 11C, 11D, 12A, 12B, 12C, 13A, 13B, 13C, 14A, 14B, 15A, and 15B depict a fixation device 100d in accordance with a fourth embodiment of the present invention. Features of FIGS. 11A, 11B, 11C, 11D, 12A, 12B, 12C, 13A, 13B, 13C, 14A, 14B, 15A, and 15B that are the same as or similar to those described previously are given the same reference numbers with the addition of the suffix "d". Description of common elements and operation similar to those in the previously described embodiments will not be repeated with respect to the fourth embodiment.

The fixation devices 100d shown in FIGS. 11A, 11B, 11C, 11D, 12A, 12B, 12C, 13A, 13B, 13C, 15A, and 15B are variations of fixation devices according to the fourth embodiment. While the first through third embodiments included deformable members 124, 124b, and 124c having a cantilevered pawl configuration, the deformable member 124d of the fourth embodiment may take the form of at least one bridge rim 124d, as shown in FIGS. 11A, 11B, 11C, 11D, 12A, 12B; 12C; 13A, 13B, 13C, 15A, and 15B. That is, the void 120d is fully enclosed within at least a portion of the rim portion 118d and the bridge rim 124d is defined therebetween. The void 120d could function as the tool receptor void 122d and accept a driving tool (not shown) with a driving head shaped to mate with at least a portion of the void 120d. The deformable member 124d of the fourth embodiment engages at least one circumferentially oriented serration 536d, which has serration anti-reverse features 537d oriented to resist force exerted in a longitudinal direction.

The bridge rim 124d, when present, is adapted to selectively deflect laterally with respect to the longitudinal axis 110d. The bridge rim 124d may extend between the top and bottom surfaces 112d and 114d and may be attached to the remainder of the head portion 104d only at laterally opposed extreme ends of the bridge rim 124d, to facilitate lateral deflection of the bridge rim 124d.

The bridge rim 124d may have any suitable shape or configuration, and can readily be designed by one of ordinary skill in the art for a desired application of the fixation device 100d without restriction to the depicted examples. The fixation device 100d shown in FIGS. 11A, 11B, 11C, and 11D includes two diametrically opposed bridge rims 124d separated laterally by the main body 116d of the head portion 104d. The fixation device 100d shown in FIGS. 12A, 12B, and 12C includes one bridge rim 124d extending a majority of the distance around a circumference of the head portion 104d. The fixation device 100d shown in FIGS. 13A, 13B, and 13C includes two diametrically opposed bridge rims 124d separated laterally by the main body 116d of the head portion 104d and being partially defined by an undulating rim portion 118d. The undulating structure of the bridge rims 124d shown in FIGS. 13A, 13B, and 13C may provide a desired spring-like structural resilience to the bridge rims, in addition to the material resilience inherently provided by the material of the bridge rims. The bridge rims 124d, like all deformable members 124d of the present invention, could be located symmetrically about the head portion 104d, such as in the diametrically opposed arrangement shown in the Figures, or could be located eccentrically or asymmetrically (not shown).

At least in part because of the "closed" (i.e., no break in the circular continuity of the rim) band-like structure of the bridge rim 124d in several variations of the fourth embodiment of the present invention, the longitudinally-oriented serrations 536, 536b, and 536c discussed in relation to the first, second, and third embodiments, respectively, may not engage the bridge rim 124d as desired without some additional structure, such as the hybrid structures of the sixth embodiment, below. Instead, at least one serration 536d of the fourth embodiment is formed circumferentially about at least a portion of the inner hole surface 534d, and each of the circumferential serrations may be spaced longitudinally from at least one other serration. As shown in at least FIG. 14B and as is the case with all embodiments of the present invention, the serrations 536d need not be matched in depth, arrangement, size, orientation, or any other attribute. It is advantageous, however, for a chosen circumferential serration 536d intended to engage with the bridge rim 124d to be smaller in diameter than at least a portion of the bridge rim so that the bridge rim must deflect laterally inward for insertion through that chosen serration. The bridge rim 124d will then expand outward after having passed through the chosen circumferential serration 536d and thereby resist longitudinal displacement of the fixation device 100d away from the bone member. In this manner, the bridge rim 124d extends to a location radially further from the longitudinal axis 110d than the location of at least a portion of the serration anti-reverse feature 537d, causing the bridge nm 124d to "enter into" the serration 536d.

In any embodiment of the present invention, the head portion 104d may include at least one protruding tooth 1144, as shown with respect to the fourth embodiment in FIGS. 11A, 11B, 11C, 11D, 12A, 12B, 12C, and 15B. The tooth 1144 may act as the holddown feature discussed previously. The tooth 1144 may be adapted, as shown in FIG. 15B, to mate with an undercut serration 536d extending circumferentially around at least a portion of the fixation hole 532d, to help prevent the fixation device 100d from displacement longitudinally with respect to the bone member. The structure of the tooth 1144 is not essential to the present invention, and the tooth could have any suitable size or position relative to the other components of the head portion 104d.

For example, at least a portion of a perimeter of the bottom surface 114d could extend further from the longitudinal axis 110d than does a corresponding portion of a perimeter of the top surface 112d, to form a more rim-like circumferential tooth or stepped portion (not shown) which could engage with the undercut serration 536d. Likewise, and similarly to the tooth 1144 depicted in the Figures, at least one portion of the rim portion 118d located longitudinally between the top and bottom surfaces 112d and 114d may define a rim extension (not shown), of any suitable shape, extending laterally outward from the main body 116d further from the longitudinal axis 110d than does a perimeter of either of the top and bottom surfaces.

It is contemplated that any provided tooth 1144 or rim extension of the present invention could extend laterally outward from the main body at or near the top surface 112, the bottom surface 114, or any point therebetween, and the tooth or rim extension could mate with one or more serrations 536d oriented circumferentially, longitudinally, laterally, or in any combination of these orientations (further discussed below with reference to the sixth embodiment).

FIGS. 16A, 16B, 16C, 17A, 17B, 17C, 17D, and 18 depict a fixation device 100e in accordance with a fifth embodiment of the present invention. Features of FIGS. 16A, 16B, 16C, 17A, 17B, 17C, 17D, and 18 that are the same as or similar to those described previously are given the same reference numbers with the addition of the suffix "e". Description of common elements and operation similar to those in the previously described embodiments will not be repeated with respect to the fifth embodiment.

The fixation device 100e of the fifth embodiment includes at least one deformable member 124e connected with the head portion. The deformable member 124e extends laterally in a direction substantially perpendicular to the longitudinal axis 110e and may be adapted to deflect laterally to engage with at least one serration 536e formed on the inner hole surface 534e. Engagement between the deformable member 124e and a serration 536e, after the deformable member 124e is deformed, helps to prevent displacement of the fixation device 100e within the fixation hole 532e.

The deformable member 124e may be deformed manually by the user with any suitable standard tool or with a custom tool such as the deformer cap 1650 shown in FIGS. 16A, 16B, 16C, 17A, 17B, 17C, 17D, and 18. The deformer cap 1650 could be removable after the deformable member 124e is deformed, or the deformer cap 1650 could be left in place to help maintain deformation of the deformable member. The decision whether to remove the deformer cap 1650 may be made by the user after consideration of factors including whether the deformable member 124e is plastically or elastically deformable.

Figure 16A:
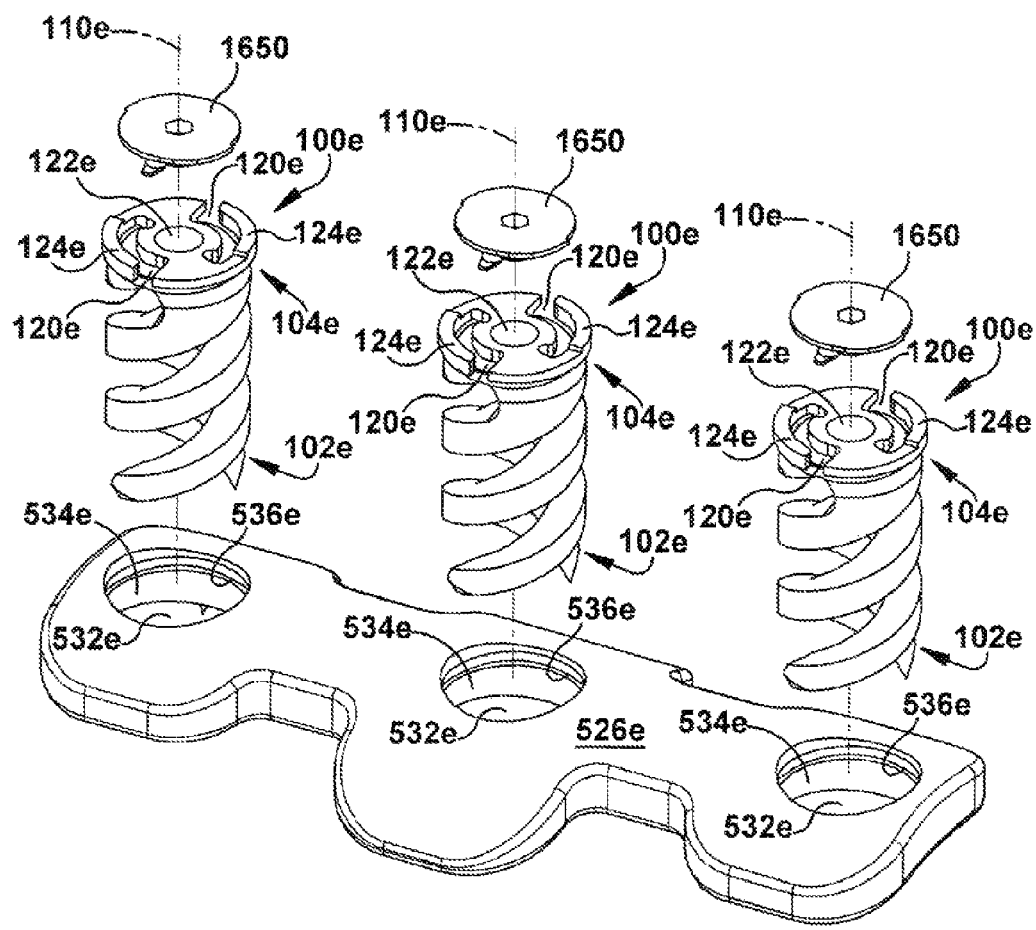
FIG. 16A is an exploded perspective view of a fifth embodiment of the present invention.
Figure 16C:
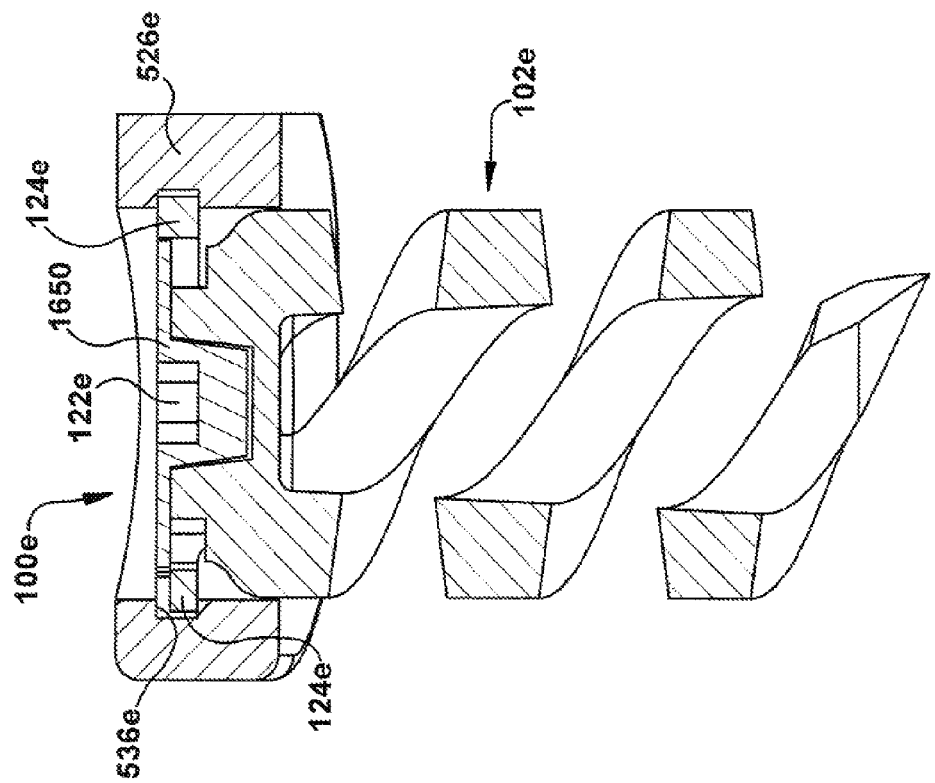
FIG. 16C is a cross-sectional view taken along line C-C in FIG. 16B.
Figure 16B:
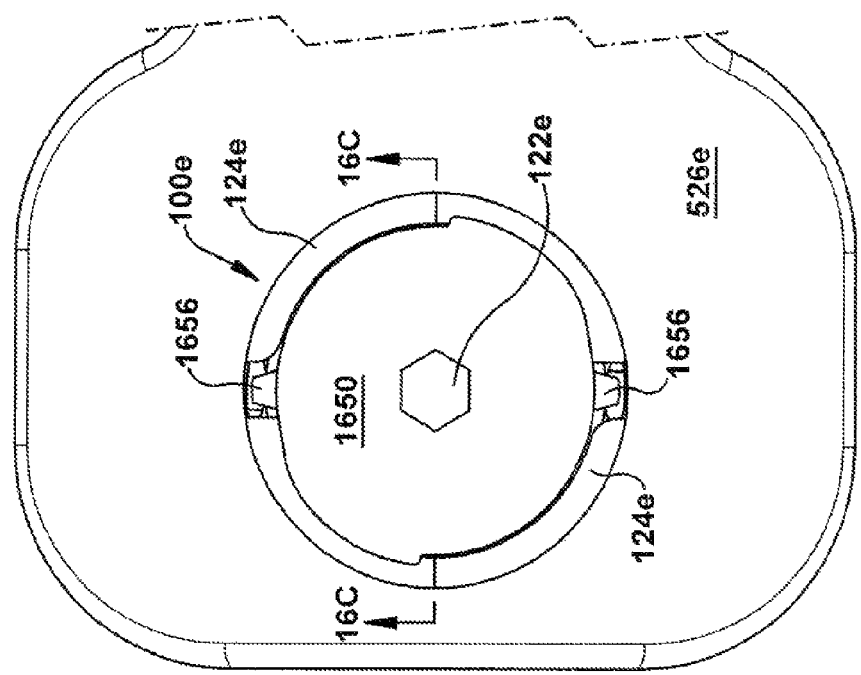
FIG. 16B is a top view of the fifth embodiment.
Figure 17A:
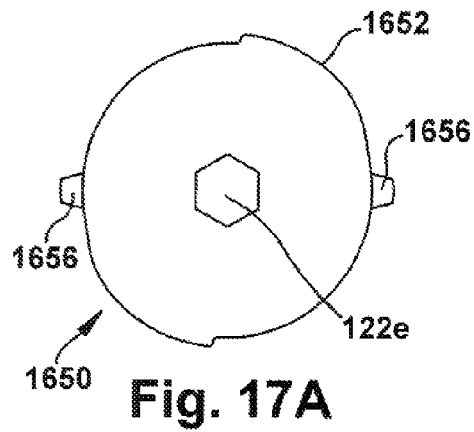
FIG. 17A is a top view of the fifth embodiment.
Figure 17B:
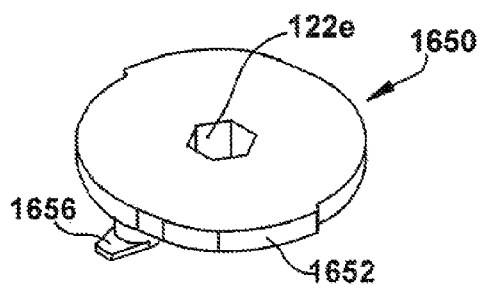
FIG. 17B is a perspective view of the fifth embodiment shown in FIG. 17A.
Figure 17C:
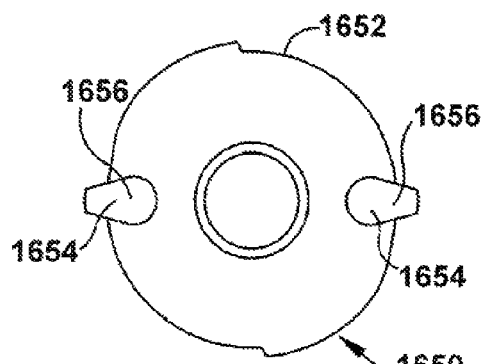
FIG. 17C is a bottom view of the fifth embodiment shown in FIG. 17A.
Figure 17D:
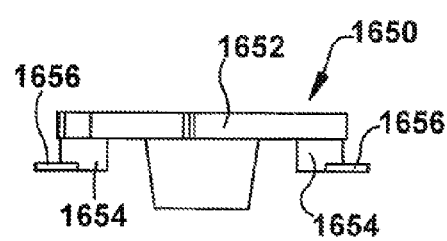
FIG. 17D is a side view of the fifth embodiment shown in FIG. 17A.

As shown in at least the perspective view of FIG. 17B, the deformer cap 1650 may include a cam profile 1652 and at least one deformer post 1654. The deformer post 1654 is adapted for insertion into a void 120e, to position the deformer cap 1650 longitudinally adjacent the head portion 104e of the fixation device 100e. The deformer cap 1650 may nest into a recessed portion of the head portion 104e, as shown in FIGS. 16A and 16B, to bring the cam profile 1652 laterally adjacent the deformable member 124e and thereby exert an outward force against the deformable member. A driving tool (not shown) is either inserted into the tool receptor void 122e, or is formed integrally with the deformer cap 1650.

When the deformer cap 1650 is rotated in a first direction by the driving tool in the fifth embodiment shown in the Figures, the cam profile 1652 presses the deformable member 124e laterally outward and into engagement with a serration 536e on the inner hole surface 534e. Concurrently, the deformer post 1654 is located within the void 120e to help in positioning the deformer cap 1650 and perhaps help prevent the deformer cap from slipping out of contact with the deformable member 124e. The deformer posts 1654 may lock into place with at least a portion of the void 120e to hold the deformer cap 1650 in place when the engagement between the deformable member 124e and the serration 536e has been accomplished The deformer cap 1650 may include structure, such as the deformer tabs 1656 shown in FIGS. 16, 17A, 17B, 17C, 17D, and 18 extending from the deformer posts 1654. The deformer tabs 1656, when present, may engage with an underneath side of the deformable member 124e and prevent the deformable member from longitudinal displacement under the deformation force applied by the deformer cap.

Figure 18:
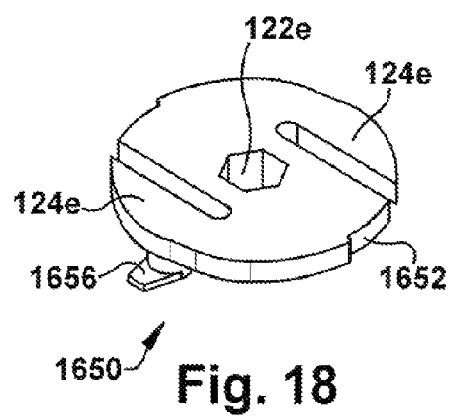
FIG. 18 is a perspective view of the fifth embodiment.
Figure 19F:
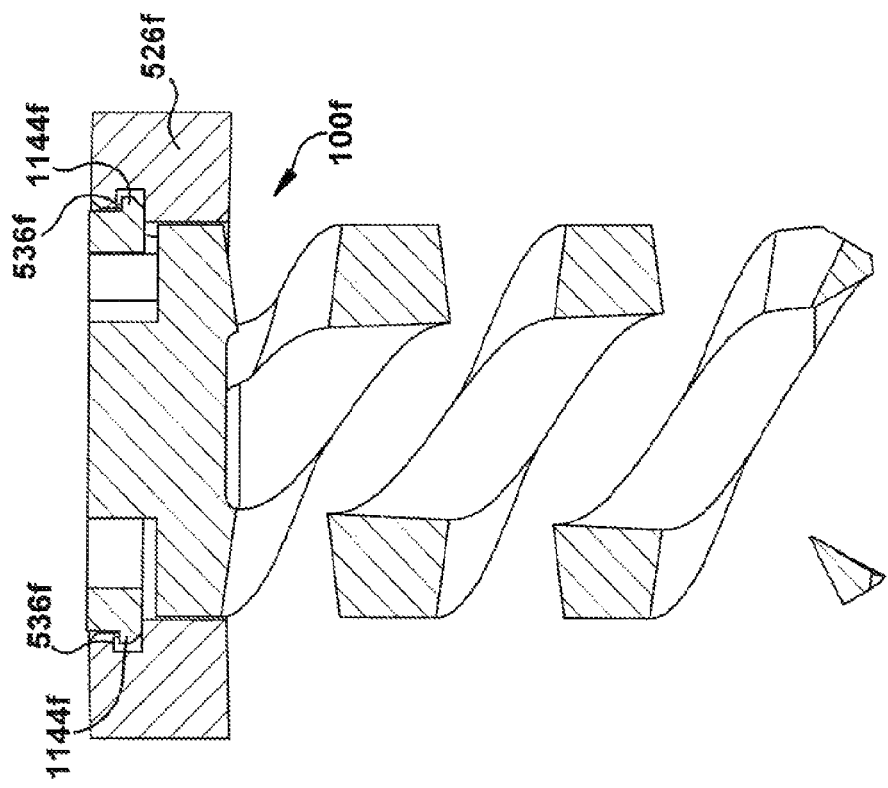
FIG. 19F is a cross-sectional view taken along line F-F in FIG. 19E.
Figure 19E:
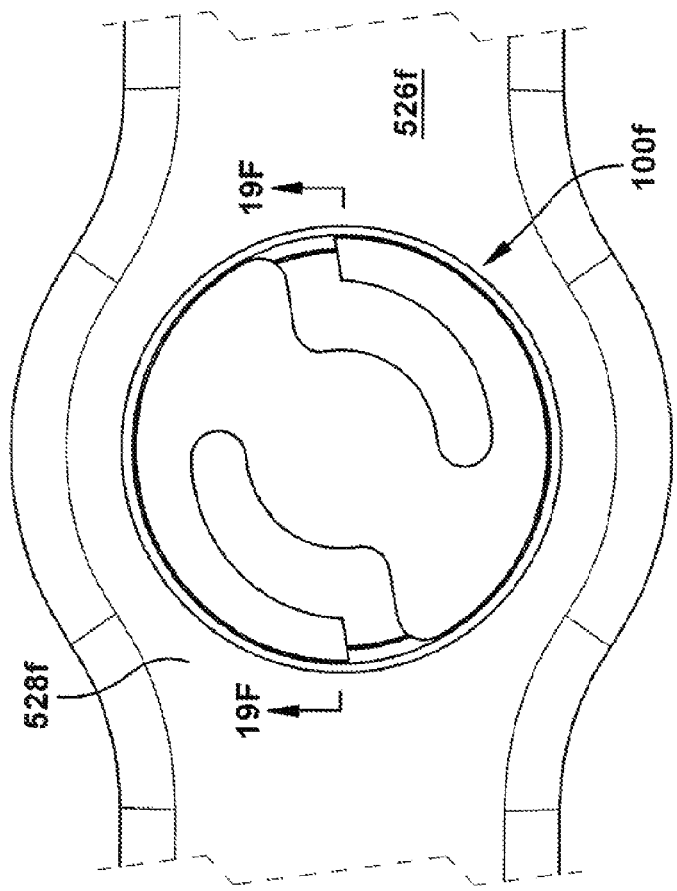
FIG. 19E is a top view of a sixth embodiment of the present invention.

Regardless of the presence of deformer tabs 1656 or similar retention structures, the deformer cap 1650 may be left in place, effectively "locking" the fixation device 100e in place within the fixation hole 532e. The deformer cap 1650 may include at least one deformable member 124e, as shown in FIG. 18, to function similarly to the deformable members 124, 124b, 124c, and 124d in the first through fourth embodiments and accordingly provide another form of resistance to displacement of the fixation device 100e from the bone member.

Optionally, and when the deformable member 124e is plastically deformable, the driving tool may be rotated in a second direction, opposite the first direction, to "unscrew" the deformer cap 1650 from the head portion 104e, thus disengaging each deformer post 1654 from the corresponding void 120e and allowing the deformer cap 1650 to be removed from the now-deformed head portion 104e of the fixation device 100e.

Instead of nesting into a recess in the head portion 104e to locate the cam profile 1652 laterally adjacent the deformable member 124e, the deformer cap 1650 may rest atop a non-recessed head portion 104e. This variation would position at least a portion of the cam profile 3652 laterally adjacent the inner hole surface 534e. In such case, the cam profile 1652 could brace against the inner hole surface 534e and thereby cause the deformer post 1654 to force the deformable member 124e outward into engagement with the serration 536e.

It is contemplated that, in the fifth embodiment of the present invention, the deformable member 124e may be adapted to deflect laterally without engaging with a serration 536e. Instead, the deformer cap 1650 may wedge the deformable member 124e against some non-serrated structure (not shown) of the plate 526e, such as a non-serrated void, to frictionally engage such structure with the deformable member.

FIGS. 19A, 19B, 19C, 19D, 19E, 19F, 19G, and 19H depict a fixation device 100f in accordance with a sixth embodiment of the present invention. Features of FIGS. 19A, 19B, 19C, 19D, 19E, 19F, 19G, and 19H that are the same as or similar to those described previously are given the same reference numbers with the addition of the suffix "f". Description of common elements and operation similar to those in the previously described embodiments will not be repeated with respect to the sixth embodiment.

The hybrid fixation device 100f of the sixth embodiment bears similarities to portions of the fixation devices 100, 100b, 100c, 100d, and 100e of each of the first through fifth embodiments. For instance, a tip 138f of at least one deformable member 124f engages with at least one longitudinally oriented serration 536f, as in at least the first embodiment, and a tooth 1144f located at the tip of the deformable member concurrently engages with at least one circumferentially oriented serration (referenced as 536f$_2$ for clarity), as in the fourth embodiment. The engagement Of the deformable member(s) 124f with the longitudinally oriented serrations 536f helps prevent rotational displacement—or "backing out"—of the fixation device: 100f with respect to the fixation hole 52f, while the engagement of the deformable members 124f with the circumferentially oriented serrations 536f$_2$ helps prevent longitudinal displacement of the fixation device 100f with respect to the fixation hole 532f. The serration anti-reverse features 537f and 537f$_2$ are provided by the longitudinally oriented serrations 536f and the circumferentially oriented serration 536f$_2$, respectively.

One of ordinary skill in the art could readily design a tooth 1144 or rim extension and corresponding serration(s) 536 to allow either of the cantilevered pawl or bridge rim types of deformable members 124 to be used interchangeably in any embodiment of the present invention, as desired. An example of such an interchangeable structure is shown by the use of a cantilevered pawl configuration with the circumferential serrations of the sixth embodiment.

FIGS. 20, 21A, 21B, 21C, and 21D depict a fixation device 100g in accordance with a seventh embodiment of the present invention. Features of FIGS. 20, 21A, 21B, 21C, and 21D that are the same as or similar to those described previously are given the same reference numbers with the addition of the suffix "g". Description of common elements and operation similar to those in the previously described embodiments will not be repeated with respect to the seventh embodiment.

Figure 20:
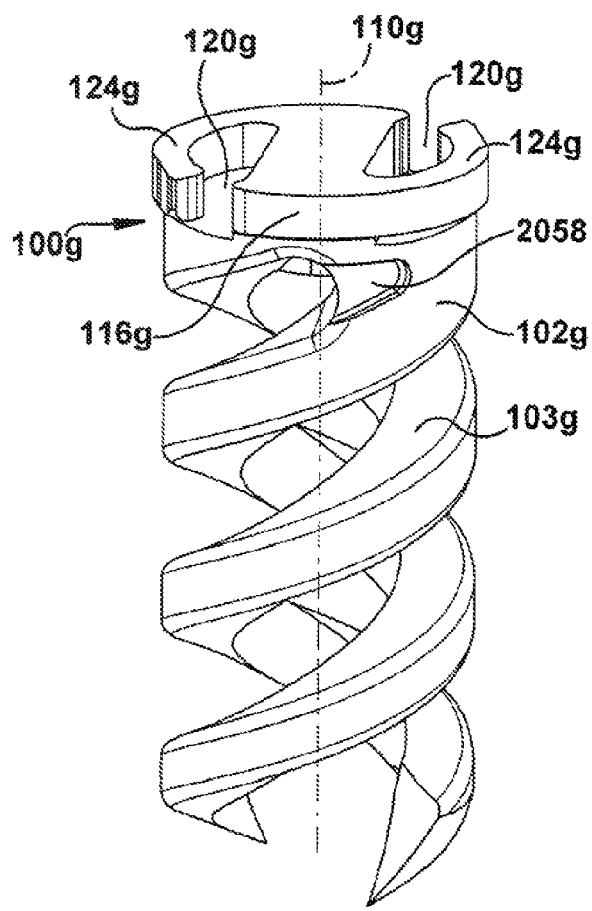
FIG. 20 is a perspective view of a seventh embodiment of the present invention.

The shaft portion 102g of the fixation device 100g, as shown in FIG. 20, includes at least one blocking notch 2058. The blocking notch 2058 may be located anywhere on the fixation device 100g and formed in any suitable manner. For example, the blocking notch 2058 is shown in FIG. 20 as partially extending into the shank 102g of the fixation device 100g. It is contemplated that the blocking notch 2058 may be of any suitable size, shape, or configuration and can readily be provided by one of ordinary skill in the art.

Figure 21A:
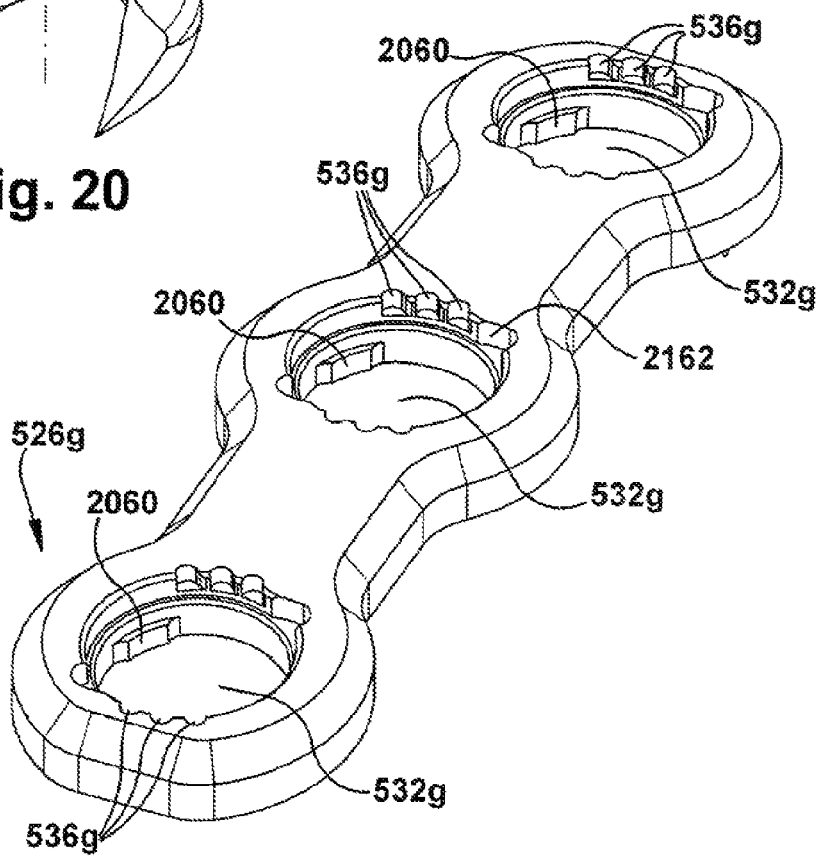
FIG. 21A is a perspective view of the seventh embodiment.

FIG. 21A depicts a plate 526g according to the seventh embodiment of the present invention. The plate 526g includes at least one fixation hole 532g (three shown), each fixation hole being adapted to receive a fixation device 100g. Each fixation hole 532g includes at least one serration 536g adapted to engage with a deformable member 124g of a corresponding fixation device 100g and thereby prevent displacement of the fixation device 100g within the fixation hole. As depicted in FIG. 21A, a plurality of serrations 536g may be oriented longitudinally, and spaced circumferentially, about the fixation hole 532g.

Each fixation hole 532g of the seventh embodiment may include at least one blocking lug 2060, as shown in FIG. 21A. The blocking lug 2060 may be located at any suitable location with respect to the fixation hole 532g. The blocking lug 2060 should be sized to allow passage of the shank 102g of the fixation device 100g through the fixation hole 532g. For example, the blocking lug 2060 could be sized to fit laterally between helical spikes 103g of a fixation device 100g and to slidably maintain that lateral relationship as the fixation device 100g is rotated in the first direction to engage the body tissue member. It is contemplated that the blocking lug 2060 may be of any suitable size, shape, or configuration and can readily be provided by one of ordinary skill in the art, but should be adapted for a desired mating relationship with the blocking notch 2058.

Figure 21B:
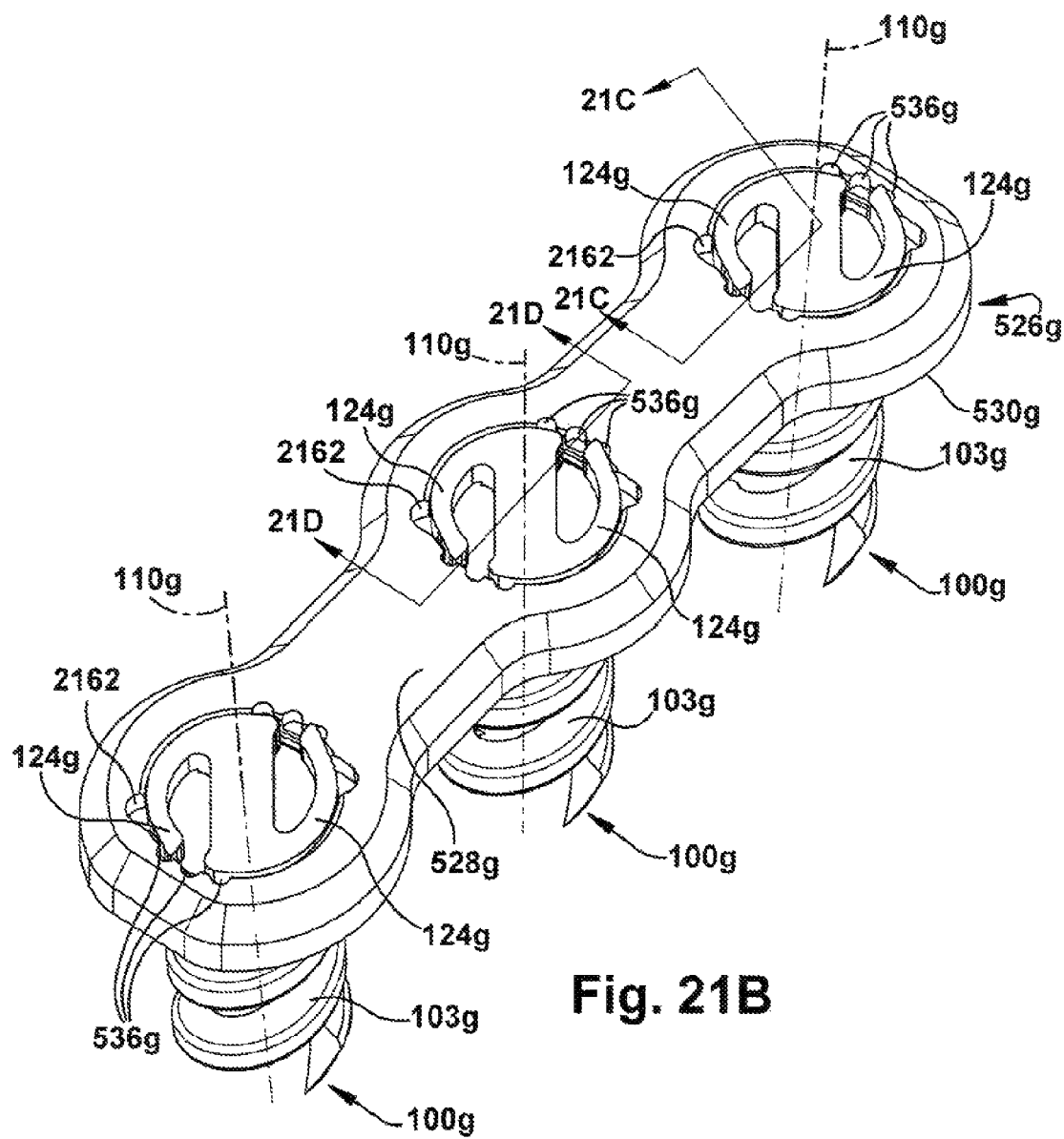
FIG. 21B is a perspective view of the seventh embodiment.

FIG. 21B depicts the plate 526g having a plurality of fixation devices 100g associated therewith. Serrations 536g need not be provided around the entire circumference of each fixation hole 532g in the seventh embodiment because the blocking lugs 2060 key or register each fixation device 100g into a known orientation during insertion of the fixation device into the fixation hole. In other words, a blocking lug 2060 extends laterally into the fixation hole 532g and prevents insertion of the fixation device 100g unless the fixation device is aligned for insertion with the blocking lug 2060 protruding laterally between one or more helical spikes 103g. Therefore, the deformable members 124g of the fixation device 100g will always engage with a serration 536g at a known location on the circumference of the fixation hole 532g.

It would be possible to provide only one serration 536g per deformable member 124g in the seventh embodiment of the present invention. However, a few serrations 536g per deformable member 124g will provide the user with a range of positions into which the fixation device 100g can be placed as desired, for greater versatility. In addition, movement of the deformable member 124g past the serrations 536g may provide an audible and/or tactile indication to the user that the fixation device 100g is approaching a position in which the blocking notch 2058 and the blocking lug 2060 will engage.

The blocking notch 2058 and blocking lug 2060 of the seventh embodiment selectively interlock responsive to a predetermined amount of rotation of the fixation device 100g in the first direction about the longitudinal axis 110g. The interlocking of the blocking notch 2058 and blocking lug 2060 is operative to substantially prevent further rotation of the fixation device 100g in the first direction. One of ordinary skill in the art can design the fixation device 100g and/or the fixation hole 532g to achieve a desired amount of rotation of the fixation device in the first direction before the interlocking stop function of the blocking notch 2058 and blocking lug 2060 is performed.

Figure 21C:
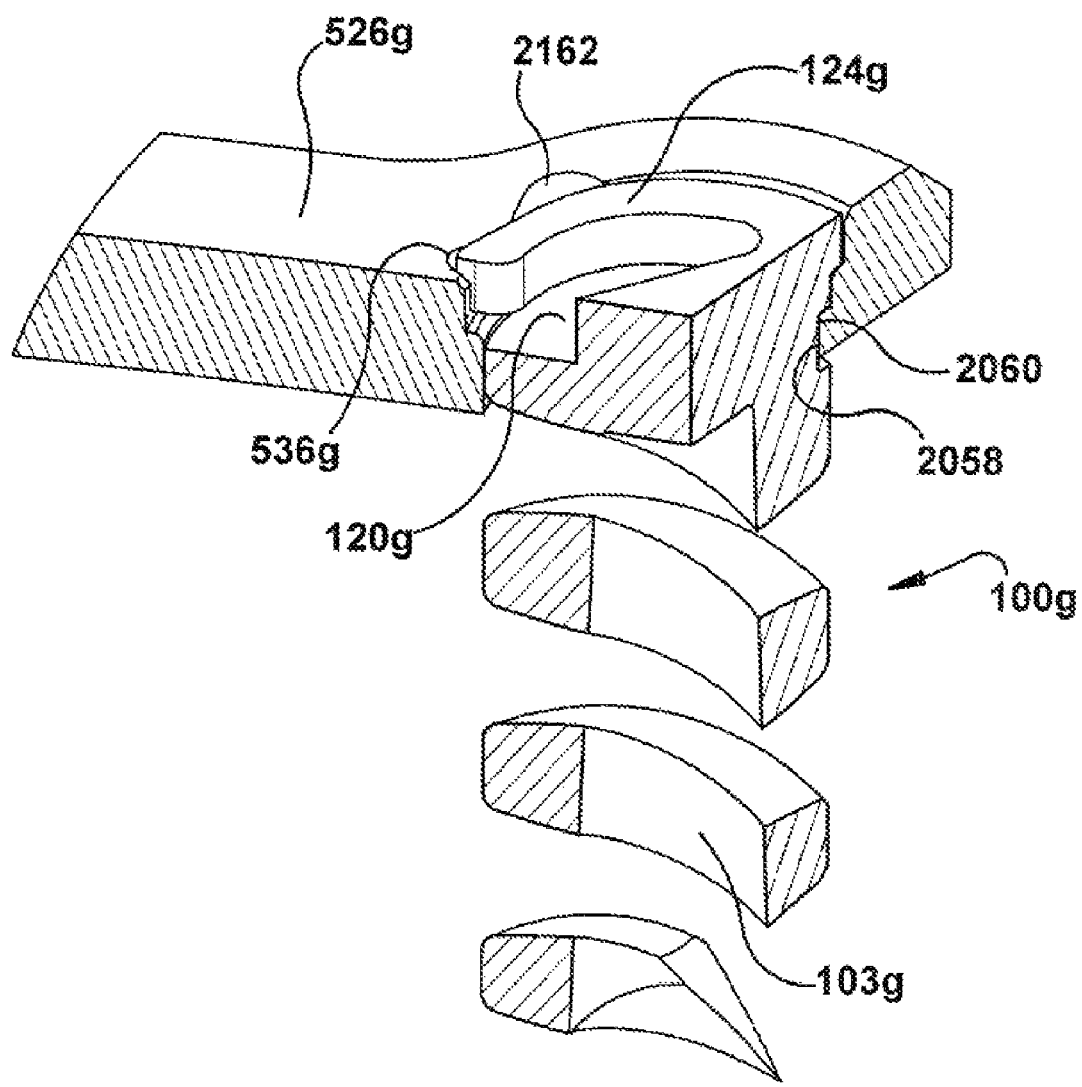
FIG. 21C is a cross-sectional view taken along line C-C in FIG. 21B.

As shown in the cross-sectional view of FIG. 21C, the blocking notch 2058 and blocking lug 2060 may be positioned and configured to meet and constrain rotation of the fixation device 100g when the fixation device has reached a maximum desired engagement position with the fixation hole 532g. Accordingly, the fixation device 100g is prevented from "bottoming out" or being overtightened into the plate 526g, thus avoiding structural damage to the fixation device and/or the plate. Similarly, since overtightening could cause coring or stripping out of the body tissue (e.g., bone) into which the fixation device 100g extends, the engagement of the blocking notch 2058 and blocking lug 2060 helps prevent potential structural damage to the body tissue, as well. This blocking action provided by the engagement of the blocking notch 2058 and blocking lug 2060 does not, however, prevent the fixation device 100g from being rotated in the second direction, opposite the first direction. The user therefore may disengage the fixation device 100g and fixation hole 532g without interference from the blocking notch 2058 and blocking lug 2060.

When engaged, the blocking notch 2058 and blocking lug 2060 prevent axial movement ("backout") of the fixation device 100g and the fixation hole 532g, in addition to the aforementioned rotation prevention. Therefore, through action of the blocking notch 2058 and blocking lug 2060, the fixation device 100g may be fully constrained from motion relative to the plate 526g.

The blocking notch 2058 and blocking lug 2060 are described herein as being associated with the fixation device 100g and the fixation hole 532g, respectively. However, one of ordinary skill in the art could readily provide a fixation device 100g with a blocking lug 2060 and a fixation hole 532g with a blocking notch 2058. In addition, any number of blocking lugs 2060 and/or blocking notches 2058 could be provided and need not exactly correspond in matched pairs.

Figure 21D:
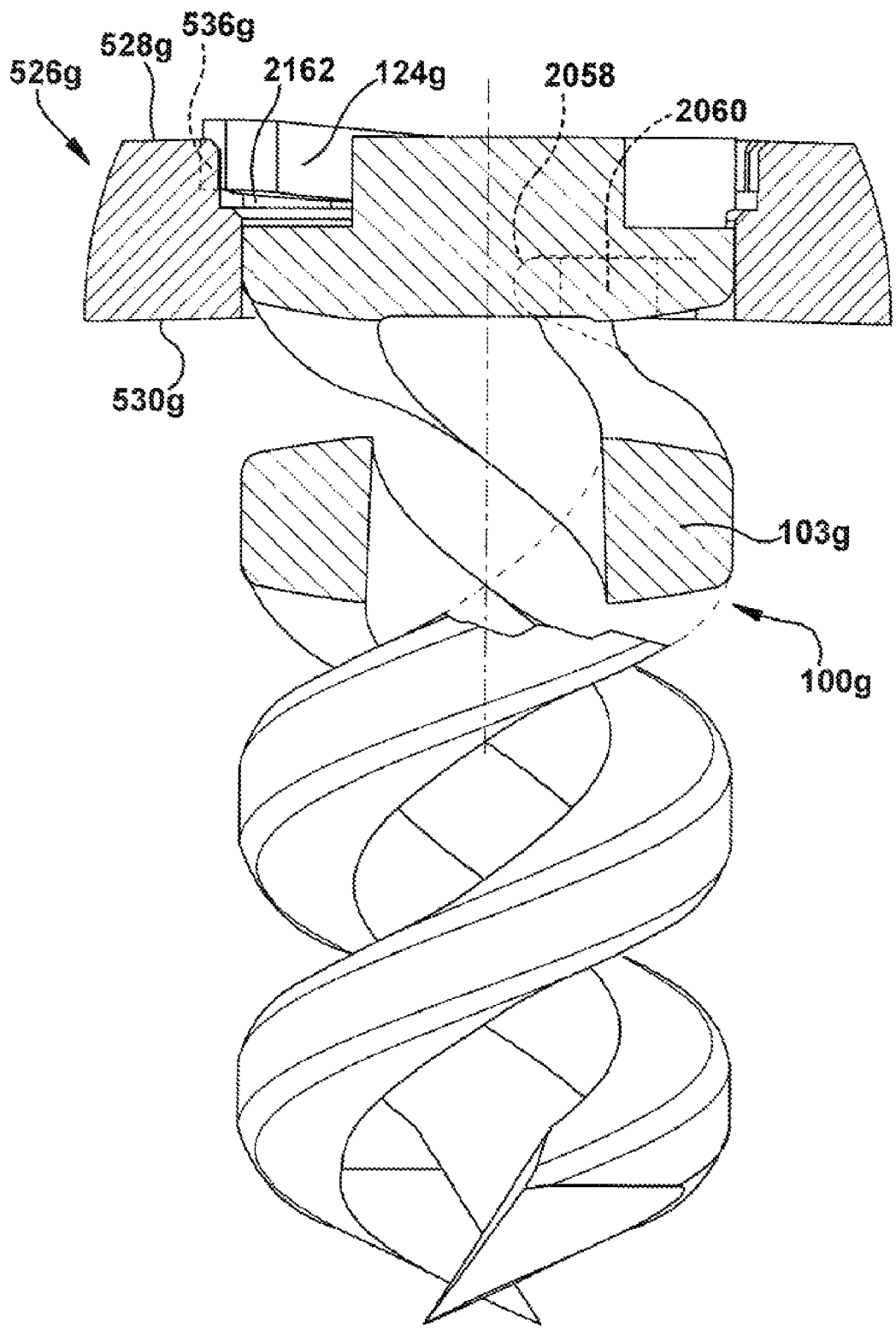
FIG. 21D is a cross-sectional view taken along line D-D in FIG. 21B.

As can be seen in the cross-sectional view of FIG. 21D, the serration 536g may be positioned to engage the deformable member 124g with a slight deflection in the longitudinal direction. This deflection may be sufficient to cause the deformable member 124g to protrude from the fixation hole 532g as shown, but the serration 536g could instead be designed to deflect the deformable member 124g longitudinally while maintaining the deformable member 124g laterally within the plate 526g. By resisting the deflection, the deformable member 124g creates a longitudinal spring force against the plate 526g. This longitudinal spring force can be used to create a steadying or bracing arrangement to hold the fixation device 100g in longitudinal contact with the plate and prevent looseness or play therebetween. When present, this spring-tightening function could be useful in avoiding small relative flexing or wiggling movements between the fixation device 100g and the plate 526g which may, over time, cause unwanted disengagement of the fixation device and the plate. Such a spring-tightening function could be used in any embodiment of the present invention in which the deformable member 124g is configured to be suitably resilient and at least one serration 536g is suitably longitudinally offset to deflect the deformable member. Alternatively, it is contemplated that a mechanical structure (not shown) may be provided to at least one of the fixation device 100g and the plate 526g, to cause the deformable member to exert the longitudinal spring force against the plate.

The seventh embodiment of the present invention also may include an access void 2162 to assist the user in selectively disengaging the fixation device 100g from the fixation hole 532g. The access void 2162, as shown in FIGS. 21A, 21B, 21C, and 21D, could be provided to accommodate a removal tool larger than could be inserted into a serration 536g. When present, the access void 2162 could extend longitudinally further into the fixation hole 532g than does the serration 536g. In such case, the removal tool could be inserted into the access void 2162 and engage with an underside of the deformable member 124g (when the deformable member is deflected longitudinally by the serrations 536g) to assist in disengaging the fixation device 100g from the fixation hole 532g.

Whether or not the deformable member 124g is deflected longitudinally, however, a removal tool could be inserted into one or more of the access void 2162 and a serration 536g and used to deflect the deformable member 124g laterally toward the longitudinal axis 110g. Once the deformable member 124g has been deflected out of engagement with the serration 536g, the removal tool and/or another toot could be used to rotate the fixation device 100g in the second direction and thereby at least partially disengage the fixation device from the fixation hole 532g as desired.

Figures 22A, 22B:
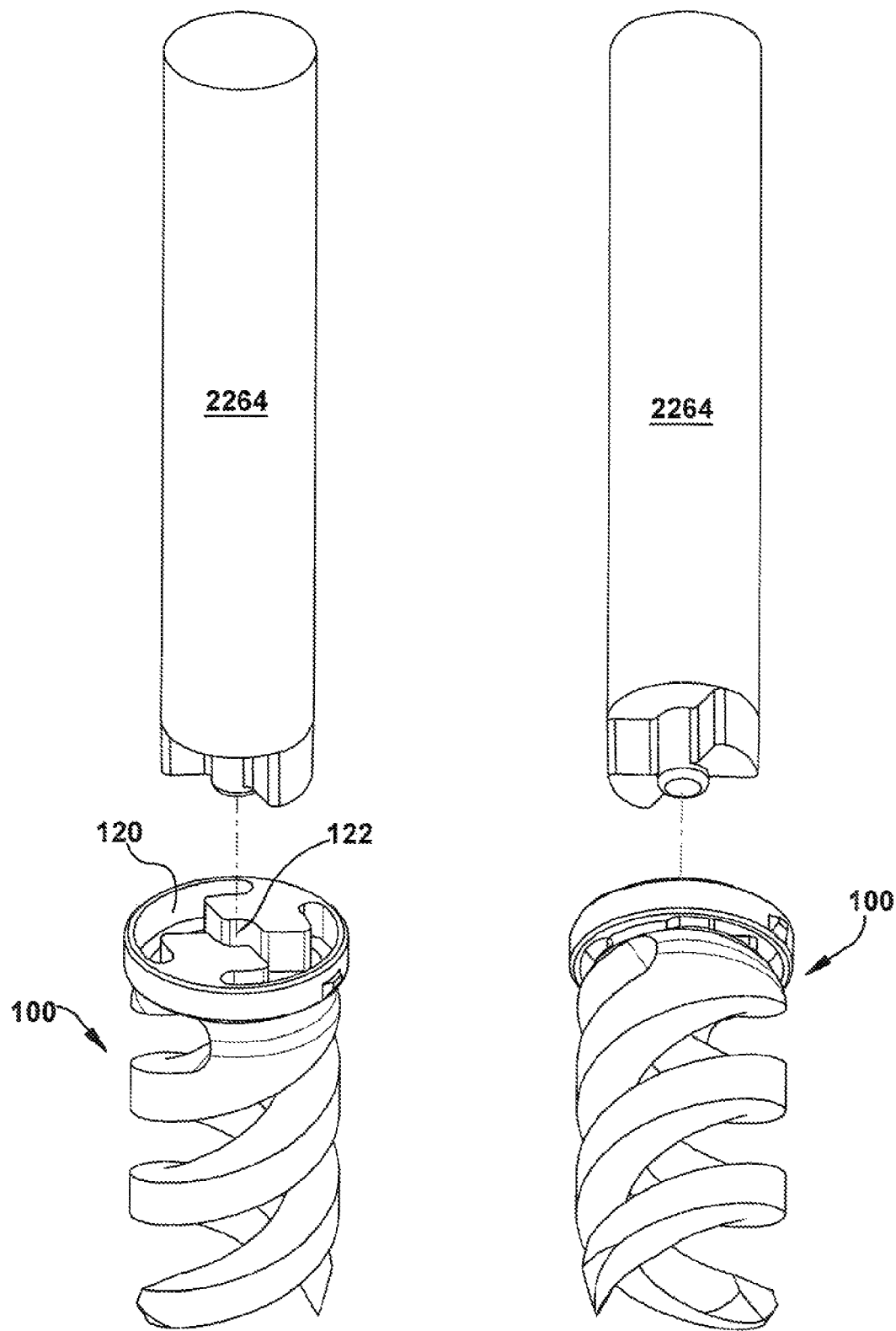
FIG. 22A is a perspective view of a driving tool for use with any of the first through seventh embodiments of the present invention.
FIG. 22B is a perspective view of a driving tool for use with any of the first through seventh embodiments of the present invention.

In use, each of the first through seventh embodiments of the present invention operates similarly. The plate 526 is placed into a desired orientation with a subject body tissue, such as a bone, of the patient. The second shank end 108 of the fixation device 100 is inserted into the fixation hole 532 and into engagement with the body tissue. A driving/insertion tool 2264, as shown in FIGS. 22A and 22B, may be provided to engage with at least one of the void 120 and the tool receptor void 122.

The head portion 104 is rotated, optionally by actuating the insertion tool 2264, in a first direction to cause the shank 102 to sink into the body tissue and the head portion to engage the plate 526. The deformable member 124, whether provided as part of the head portion 104 or as part of a retainer cap 640, deformer cap 1650, or other structure, is deflected away from an initial position. The deformable member 124 engages at least one serration 536 to help prevent the fixation device 100 from displacement within the fixation hole 532, optionally including helping prevent rotation within the fixation hole 532 in a second direction opposite the first direction. If a tooth 1144 or other holddown structure is provided on one of the fixation device 100 and the plate 526, such additional structure engages with the corresponding structure of the other of the fixation device 100 and the plate 526 to further help secure the fixation device 100 in a desired manner.

Should the user wish to displace the fixation device 100 from the fixation hole 532 after installation, whether during another phase of the installation or at some post-installation future time, a removal tool (not shown), such as mat described above with reference to the seventh embodiment, could be used to deflect the deformable member 124 out of engagement with the serration 536. The head portion 104 can then be rotated in the second direction and backed out of engagement with the bone member. The design of the removal tool will depend upon the structure of the head portion 104—i.e., the specific orientation and dimension of the deformable member 124, whether a tooth 1144 or other holddown structure is provided, and the nature of that holddown structure. A suitable removal tool can be readily designed for a particular application by one of ordinary skill in the art. For example, a removal hole (not shown) could be provided near the tip 138 of the deformable member 124, and a needle-nose pliers could engage with the removal hole to pull the deformable member 124 laterally out of engagement with the serration 536.

While aspects of the present invention have been particularly shown and described with reference to the preferred embodiment above, it will be understood by those of ordinary skill in the art that various additional embodiments may be contemplated without departing from the spirit and scope of the present invention. For example, the tool receptor void 122 may be replaced with a tool mating extension (not shown) to allow the fixation device 100 to mate with a driving tool in a male-to-female manner. The void 120 and tool receptor void 122 functions could be combined into a single void structure in any of the embodiments. Each of the void 120 and the tool receptor void 122 can have any suitable constant or variable longitudinal cross-section. Any of the configurations or features of the first through seventh embodiments described above could be combined for use in a specific application. An adhesive, solder, lock washer, or other engagement enhancing device could be provided to help maintain a desired engagement between structures of the fixation system. The deformable member 124 of any embodiment could have a different cross-section than those shown, in order to engage with a serration 536 in a desired manner. Any suitable material or combination of materials could be used to form the components of the fixation system, though biocompatible metals or plastics are preferred for implantation into patients. The fixation system could include an interference/frictional fit between the plate 526 and fixation device 100. The retainer stud 642 of the second embodiment could be shaped as needed to mate with any type of tool engagement void 122b and thereby retrofit existing bone screws for use with a fixation system according to the present invention. The plate 526 could contain any number and orientation of contoured surfaces to engage with a body tissue in a desired manner, though the contours of the plate may dictate design considerations for the fixation hole 532 and/or the fixation device 100. However, a device or method incorporating such an embodiment should be understood to fall under the scope of the present invention as determined based upon the claims below and any equivalents thereof.

The method and apparatus of certain embodiments of the present invention, when compared with other apparatus and methods, may have the advantages of: resisting toggling, resisting backing out, engaging firmly with a plate or other corrective device, being usable in a timely and efficient manner, and being economical to manufacture and use. Such advantages are particularly worthy of incorporating into the design, manufacture, and operation of body tissue fixation systems.

Other aspects, objects, and advantages of the present invention can be obtained from a study of the drawings, the disclosure, and the appended claims.

Having described the invention, we claim:

1. A body tissue fixation apparatus, comprising:
a plate having oppositely disposed outer and tissue-contacting surfaces, and at least one fixation hole extending between the outer and tissue-contacting surfaces along a longitudinal axis, the fixation hole being defined in part by an inner hole surface having at least one serration, the serration having a serration anti-reverse feature, the serration being at least one of:
formed longitudinally with respect to the inner hole surface and extending longitudinally at least a portion of the distance between the outer and tissue-contacting surfaces of the plate, the serration anti-reverse feature being oriented to resist force exerted in a circumferential direction with respect to the longitudinal axis, and
formed laterally with respect to the inner hole surface and extending radially with respect to the longitudinal axis, the serration anti-reverse feature being oriented to resist force exerted in a circumferential direction with respect to the longitudinal axis;
the plate being adapted for affixation to at least one body tissue member;
at least one fixation device having a shank and a head portion, the shank being insertable through the fixation hole in the plate to affix the plate to the body tissue member upon rotation of the head portion in a first rotation direction; and
at least one deformable member connected to the head portion, the deformable member extending laterally in a direction substantially perpendicular to the longitudinal axis and being adapted to deflect due to contact with at least one serration during rotation of the head portion to engage with at least one serration anti-reverse feature formed on the inner hole surface, wherein engagement between the deformable member and the serration anti-reverse feature resists rotation of the fixation device within the fixation hole in a second rotation direction opposite the first rotation direction.

2. The body tissue fixation apparatus of claim 1, wherein the deformable member is formed as a single piece with the head portion.

3. The body tissue fixation apparatus of claim 1, wherein the shank includes at least one of a threaded cylindrical post and one or more helical spikes.

4. The body tissue fixation apparatus of claim 1, wherein the deformable member is adapted to exert a spring force laterally outward from the longitudinal axis to urge the deformable member into engagement with at least one serration to prevent the fixation device from movement away from the body tissue member in at least one of a parallel and a rotational direction with respect to the longitudinal axis.

5. The body tissue fixation apparatus of claim 1, wherein the deformable member is adapted to exert a longitudinal spring force against the plate to hold the fixation device in longitudinal contact with the plate.

6. The body tissue fixation apparatus of claim 5, wherein at least one serration is positioned on the inner hole surface to cause the deformable member to exert the longitudinal spring force against the plate.

7. The body tissue fixation apparatus of claim 1, wherein the deformable member is adapted to deflect laterally to engage with at least one serration formed on the inner hole surface.

8. The body tissue fixation apparatus of claim 1, wherein the deformable member is adapted to deflect longitudinally to engage with at least one serration formed on the inner hole surface.

9. The body tissue fixation apparatus of claim 1, wherein the fixation hole includes an undercut serration extending circumferentially around at least a portion of the fixation hole, the serration having a serration anti-reverse feature oriented to resist force exerted in a longitudinal direction, the head portion including at least one protruding rim extension adapted to engage with the undercut serration to help prevent the fixation device from displacement longitudinally with respect to the body tissue member.

10. The body tissue fixation apparatus of claim 2, wherein the head portion includes planar top and bottom surfaces spaced apart along the longitudinal axis by a main body, the main body being bounded laterally by a rim portion, and the rim portion at least partially defines the at least one deformable member.

11. The body tissue fixation apparatus of claim 10, wherein the deformable member is a cantilevered pawl extending between the top and bottom surfaces.

12. The body tissue fixation apparatus of claim 10, wherein the deformable member is a bridge rim extending between the top and bottom surfaces.

13. The body tissue fixation apparatus of claim 1, wherein the shank is insertable through the fixation hole in the plate to affix the plate to the body tissue member upon rotation of the head portion in the first rotation direction, wherein engagement between the deformable member and at least one serration anti-reverse feature helps prevent the fixation device from rotation within the fixation hole in the second rotation direction.

14. The body tissue fixation apparatus of claim 1, wherein the deformable member is plastically deformable.

15. The body tissue fixation apparatus of claim 1, wherein the deformable member is elastically deformable.

16. The body tissue fixation apparatus of claim 1, wherein the plate includes a chosen one of a blocking notch and a blocking lug, and the fixation device includes another one of the blocking notch and the blocking lug, the blocking notch and blocking lug selectively interlocking responsive to a predetermined amount of rotation of the fixation device in the first rotation direction, the interlocking of the blocking notch and blocking lug being operative to substantially prevent at least one of further rotation of the fixation device in the first direction and longitudinal motion of the fixation device with respect to the plate.

17. The body tissue fixation apparatus of claim 2, wherein the head portion includes planar top and bottom surfaces spaced apart along the longitudinal axis by a main body, the head portion includes at least one void extending longitudinally through the main body between the top and bottom surfaces, and the void defines at least a portion of the deformable member.

18. The body tissue fixation apparatus of claim 17, wherein a cross-sectional shape of the void varies responsive to a longitudinal positioning of a cross-section with respect to the main body.

19. The body tissue fixation apparatus of claim 16, wherein the blocking lug prevents the fixation device from insertion to a maximum desired engagement position within the fixation hole unless the fixation device is registered by at least one of the blocking notch and the blocking lug into a predetermined orientation with respect to the fixation hole during rotation of the fixation device in the first direction.

20. A body tissue fixation apparatus, comprising:
a plate having oppositely disposed outer and tissue-contacting surfaces, and at least one fixation hole extending between the outer and tissue-contacting surfaces along a longitudinal axis, the fixation hole being defined in part by an inner hole surface having at least one serration;
the plate being adapted for affixation to at least one body tissue member;
at least one fixation device having a shank and a head portion, the shank being insertable through the fixation hole in the plate to affix the plate to the body tissue member upon rotation of the head portion; and
at least one deformable member formed as a single piece with the head portion, the deformable member extending laterally in a direction substantially perpendicular to the longitudinal axis and being adapted to engage with at least one serration formed on the inner hole surface, wherein engagement between the deformable member and the serration helps to prevent displacement of the fixation device within the fixation hole; wherein
the shank is insertable through the fixation hole in the plate to affix the plate to the body tissue member upon rotation of the head portion in a first rotation direction, and engagement between the deformable member and the serration resists rotation of the fixation device within the fixation hole in a second rotation direction opposite the first rotation direction.

21. The body tissue fixation apparatus of claim 20, wherein at least one serration is formed circumferentially about at least a portion of the inner hole surface, the serration has a serration anti-reverse feature oriented to resist force exerted in a longitudinal direction, and the deformable member, when engaged with the serration, extends to a location radially further from the longitudinal axis than at least a portion of the serration anti-reverse feature is located.

22. The body tissue fixation apparatus of claim 20, wherein at least one serration is formed longitudinally with respect to the inner hole surface and extends longitudinally at least a portion of the distance between the outer and tissue-contacting surfaces of the plate, and the serration includes a serration anti-reverse feature oriented to resist force exerted in a circumferential direction with respect to the longitudinal axis, and the deformable member, when engaged with the serration, extends to a location radially further from the longitudinal axis than at least a portion of the serration anti-reverse feature is located.

23. The body tissue fixation apparatus of claim 20, wherein at least one serration is formed laterally with respect to the inner hole surface and extends radially with respect to the longitudinal axis, and the serration includes a serration anti-reverse feature oriented to resist force exerted in a circumferential direction with respect to the longitudinal axis, and the deformable member, when engaged with the serration, extends to a location longitudinally further from the outer surface of the plate than at least a portion of the serration anti-reverse feature is located.

24. The body tissue fixation apparatus of claim 20, wherein the plate includes a chosen one of a blocking notch and a blocking lug, and the fixation device includes another one of the blocking notch and the blocking lug, the blocking notch and blocking lug selectively interlocking responsive to a predetermined amount of rotation of the fixation device in a first rotation direction about the longitudinal axis, the interlocking of the blocking notch and blocking lug being operative to substantially prevent at least one of further rotation of the fixation device in the first rotation direction and longitudinal motion of the fixation device with respect to the plate.

25. The body tissue fixation apparatus of claim 24, wherein the blocking lug prevents the fixation device from insertion to a maximum desired engagement position within the fixation hole unless the fixation device is registered by at least one of the blocking notch and the blocking lug into a predetermined orientation with respect to the fixation hole during rotation of the fixation device in the first direction.

* * * * *